(12) United States Patent
Higginson

(10) Patent No.: US 11,657,915 B2
(45) Date of Patent: *May 23, 2023

(54) SYSTEM AND METHODS FOR ASSET TRACKING

(71) Applicant: Phoenix Children's Hospital, Inc., Phoenix, AZ (US)

(72) Inventor: David Higginson, Phoenix, AZ (US)

(73) Assignee: PHOENIX CHILDREN'S HOSPITAL, INC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/586,164

(22) Filed: Jan. 27, 2022

(65) Prior Publication Data
US 2022/0148719 A1    May 12, 2022

Related U.S. Application Data

(63) Continuation of application No. 16/861,046, filed on Apr. 28, 2020, now Pat. No. 11,322,252.

(51) Int. Cl.
| | | |
|---|---|---|
| G16H 40/40 | (2018.01) | |
| H04W 4/029 | (2018.01) | |
| G16H 50/20 | (2018.01) | |
| H04W 4/06 | (2009.01) | |
| H04B 17/318 | (2015.01) | |

(52) U.S. Cl.
CPC ............ *G16H 40/40* (2018.01); *G16H 50/20* (2018.01); *H04B 17/318* (2015.01); *H04W 4/029* (2018.02); *H04W 4/06* (2013.01)

(58) Field of Classification Search
CPC ...... G16H 40/40; G16H 50/20; H04B 17/318; H04W 4/029; H04W 4/06
See application file for complete search history.

(56) References Cited

U.S. PATENT DOCUMENTS

| | | | |
|---|---|---|---|
| 10,056,159 B1 * | 8/2018 | Patel | H04W 64/00 |
| 10,231,078 B1 * | 3/2019 | Swart | H04L 67/12 |
| 10,488,910 B1 * | 11/2019 | Cannell | H04W 4/20 |
| 10,667,107 B2 * | 5/2020 | Bhaumik | G08B 21/22 |

(Continued)

FOREIGN PATENT DOCUMENTS

DE    102012224391 A1 *  7/2014  ............. G08C 17/02

*Primary Examiner* — Chico A Foxx
(74) *Attorney, Agent, or Firm* — Messner Reeves LLP

(57) ABSTRACT

An asset tracking system may include a bridge device that wirelessly receives beacon data from one or several beacons that are disposed at respective devices, equipment, furniture, people, and the like. The bridge device may send the beacon data to a server via a communication network. The server may analyze the beacon data, such that the locations of people or objects may be estimated and monitored, and/or sensor data corresponding to measurable attributes of people or objects may be accumulated and monitored. The location of the bridge device may be estimated using signal strength measurements of beacon signals received from room beacons in combination with corresponding room identifiers. Alerts may be sent by the server to a user device responsive to the server determining that a person or object is in an unauthorized location and/or that a value of monitored sensor data exceeds a threshold.

20 Claims, 8 Drawing Sheets

(56) References Cited

U.S. PATENT DOCUMENTS

| | | | |
|---|---|---|---|
| 2013/0253480 A1* | 9/2013 | Kimball | A61B 17/320092 606/1 |
| 2016/0012196 A1* | 1/2016 | Mark | G16H 40/40 705/2 |
| 2016/0029160 A1* | 1/2016 | Theurer | G16Z 99/00 455/456.1 |
| 2016/0234649 A1* | 8/2016 | Finnerty | H04W 4/80 |
| 2017/0228566 A1* | 8/2017 | Sengstaken, Jr. | G06K 19/0717 |
| 2017/0340221 A1* | 11/2017 | Cronin | A61B 5/02438 |
| 2018/0096292 A1* | 4/2018 | DeBusk | G16H 40/20 |
| 2018/0110475 A1* | 4/2018 | Shaya | H04W 12/033 |
| 2018/0349939 A1* | 12/2018 | Setchell | G06V 20/52 |
| 2019/0326015 A1* | 10/2019 | Cannell | G16H 40/20 |
| 2021/0185485 A1* | 6/2021 | Deixler | H04W 84/18 |

\* cited by examiner

SYSTEM AND METHODS FOR ASSET TRACKING

CROSS-REFERENCE TO RELATED APPLICATIONS

This application is a continuation of and incorporates by reference U.S. patent application Ser. No. 16/861,046 entitled "SYSTEM AND METHODS FOR ASSET TRACKING" and filed on Apr. 28, 2020.

BACKGROUND

Modern hospitals and clinics utilize a wide variety of medical equipment and consumables. While the large number of medical devices and consumables available in such hospitals allows medical professionals to provide high quality healthcare using cutting edge technologies, the large volume of such items that must be dealt with on a daily basis can be cumbersome. For example, in a survey of around 1,000 nurses, more than one-third indicated that they spend at least an hour during an average shift attempting to find the medical devices and consumables that they need to do their job.

Asset tracking technology is now available to healthcare organizations and other industries to monitor the locations of physical assets. However, conventional asset tracking systems generally use proprietary hardware to tag and track physical assets, with conventional installations costing as much as $400,000 per year.

Thus, there is a need for improved, cost-effective asset tracking systems.

SUMMARY

Embodiments of the present invention provide an asset tracking system that utilizes tags and electronic bridge devices to determine the location of various equipment, persons, or other assets. The asset tracking system may be implemented in a healthcare setting, and may be used to track the locations of patients, medical devices, and other healthcare organization property. In some embodiments, additional information may be tracked using the asset tracking system, such as medical data (e.g., vital signs) for patients and temperature data for temperature-controlled objects (e.g., refrigerators and the like).

In an example embodiment, a tracking system may include a first beacon configured to wirelessly broadcast a first beacon signal including first beacon data, a second beacon configured to wirelessly broadcast a second beacon signal including second beacon data, and electronic bridge device configured to receive the first beacon signal and the second beacon signal and store the first beacon data and the second beacon data. The tracking system may also include a server in electronic communication with the electronic bridge device. The server may include a processor and a memory device configured to store computer-readable instructions which, when executed, cause the processor to receive the first beacon data and the second beacon data from the electronic bridge device, analyze the first beacon data and the second beacon data to identify associations between the first beacon data and the second beacon data, and store the first beacon data, the second beacon data, and the identified associations in the memory device.

In some embodiments, the first beacon may include a room beacon disposed at a fixed location within a first room. The first beacon data may include room beacon data. The computer-readable instructions, when executed, may cause the processor to determine a location of the electronic bridge device based on room beacon data, and associate the second beacon data with the location of the electronic bridge device.

In some embodiments, the room beacon data may include a room identifier, and the computer-readable instructions, when executed, may cause the processor to reference the room identifier against a first database of the memory device to determine the location. The first database may define a first plurality of associations between room identifiers and locations. The location may correspond to the first room.

In some embodiments, the second beacon may include a patient beacon that is worn by a patient. The second beacon data may include a patient identifier associated with the patient. The computer-readable instructions may cause the processor to reference the patient identifier against a second database of the memory device to identify the patient, the second database defining a second plurality of associations between patient identifiers and patients, and update a third database of the memory device to associate the patient with the location of the electronic bridge device.

In some embodiments, the second beacon may include an equipment beacon that is disposed on a medical device. The second beacon data may include an equipment identifier associated with the medical device. The computer-readable instructions may cause the processor to reference the equipment identifier against a second database of the memory device to identify the medical device, the second database defining a second plurality of associations between equipment identifiers and equipment, and update a third database of the memory device to associate the medical device with the location of the electronic bridge device.

In some embodiments, the room beacon data may be first room beacon data. The electronic bridge device may be configured to determine a first received signal strength indicator (RSSI) value corresponding to a first received signal strength of the first room beacon signal as measured by the electronic bridge device. The electronic bridge device may be configured to send the first RSSI value to the server. The tracking system may include a second room beacon disposed at a second fixed location within a second room, the second room beacon being configured to wirelessly broadcast a second room beacon signal including second room beacon data that includes a second room identifier associated with the second room. The electronic bridge device may be configured to determine a second RSSI value corresponding to a second received signal strength of the second room beacon signal as measured by the electronic bridge device. The electronic bridge device may be configured to send the second RSSI value and the second room beacon data to the server. The computer-readable instructions, when executed, may cause the processor to compare the first RSSI value to the second RSSI value, determine that the first RSSI value exceeds the second RSSI value, and update a third database stored in the memory device to set the first room as the location of the electronic bridge device.

In some embodiments, the tracking system may include a temperature sensor coupled to the first beacon and configured to generate temperature data. The first beacon may receive the temperature data from the temperature sensor. The first beacon data may include the temperature data and a temperature sensor beacon identifier. The temperature data generated by the temperature sensor may include ambient temperature data that includes ambient temperature values measured within a temperature-controlled device. The temperature-controlled device may be associated with the temperature sensor beacon identifier. The computer-readable instructions, when executed, may cause the processor to reference the temperature sensor beacon identifier against a first database of the memory device to identify the temperature-controlled device, the first database defining a plurality of associations between temperature sensor identifiers and equipment including temperature-controlled devices, identify the temperature data of the first beacon data, update a second database of the memory device to define the temperature data as being associated with the temperature-controlled device, determine, based on the temperature data, that a predetermined threshold temperature value at the temperature-controlled devices has been exceeded, and cause an alert to be sent to a user device, the alert indicating that the predetermined threshold temperature value has been exceeded.

In some embodiments, the tracking system may include a diagnostic device configured to generate diagnostic data that includes measurements of one or more vital signs of a patient that are measured by the diagnostic device. The diagnostic device may be coupled to the first beacon. The first beacon may include a diagnostic beacon. The first beacon data may include diagnostic beacon data that includes the diagnostic data generated by the diagnostic device and that includes an equipment identifier associated with the diagnostic device.

In some embodiments, the computer-readable instructions may cause the processor to reference the equipment identifier against a first database of the memory device to identify the diagnostic device, the first database defining a plurality of associations between equipment identifiers and equipment including diagnostic devices, identify a patient associated with the diagnostic device, identify the diagnostic data within the diagnostic beacon data, update a second database of the memory device to define the diagnostic data as being associated with both the diagnostic device and the patient, determine, based on the diagnostic data, that a diagnostic data value has exceeded a predetermined threshold, and cause an alert to be sent to a user device, the alert indicating that the predetermined threshold has been exceeded.

In some embodiments, the electronic bridge device may be wirelessly coupled to the first beacon and to the second beacon via at least one wireless personal area network. The electronic bridge device may be communicatively coupled to the server via a wide area network including the internet.

In an example embodiment, a method may include steps of wirelessly broadcasting, by a first beacon, a first beacon signal including first beacon data, wirelessly broadcasting, by a second beacon, a second beacon signal including second beacon data, receiving, by an electronic bridge device, the first beacon signal and the second beacon signal, storing, by the electronic bridge device, the first beacon data and the second beacon data in a first memory device of the electronic bridge device, receiving, by a server in electronic communication with the electronic bridge device, the first beacon data and the second beacon data from the electronic bridge device, analyzing, by the server, the first beacon data and the second beacon data to identify associations between the first beacon data and the second beacon data, and storing, by the server, the first beacon data, the second beacon data, and the identified associations in a second memory device of the server.

In some embodiments, the first beacon may include a room beacon disposed at a fixed location within a first room, and the first beacon data may include room beacon data that includes a room identifier associated with the first room. The method may further include steps of referencing, by the server, the room identifier against a first database of the second memory device to determine a location of the electronic bridge device, the first database defining a first plurality of associations between room identifiers and locations, the location corresponding to the first room, and associating, by the server, the second beacon data with the location of the electronic bridge device.

In some embodiments, the second beacon may include a patient beacon that is worn by a patient. The second beacon data may include a patient identifier associated with the patient. The method may further include steps of referencing, by the server, the patient identifier against a second database of the second memory device to identify the patient, the second database defining a second plurality of associations between patient identifiers and patients, and updating, by the server, a third database of the second memory device to set a location of the patient to be the location of the electronic bridge device.

In some embodiments, the second beacon may include an equipment beacon that is disposed on a medical device. The second beacon data may include an equipment identifier associated with the medical device. The method may include steps of referencing, by the server, the equipment identifier against a second database of the second memory device to identify the medical device, the second database defining a second plurality of associations between equipment identifiers and equipment, and updating, by the server, a third database of the second memory device to set a location of the medical device to be the location of the electronic bridge device.

In some embodiments, the room beacon data may be first room beacon data and the method may further include steps of measuring, by the electronic bridge device, a first signal strength at which the first room beacon signal is received, generating, by the electronic bridge device, a first received signal strength indicator (RSSI) value based on the first signal strength, wirelessly broadcasting, by a second room beacon disposed at a second fixed location within a second room, a second room beacon signal including second room beacon data that includes a second room identifier associated with the second room, receiving, by the electronic bridge device, the second room beacon signal from the second room beacon, measuring, by the electronic bridge device, a second signal strength at which the second room beacon signal is received, generating, by the electronic bridge device, a second received signal strength indicator (RSSI) value based on the second signal strength, sending, by the electronic bridge device, the second room beacon data to the server, sending, by the electronic bridge device, the first RSSI value and the second RSSI value to the server, comparing, by the server, the first RSSI value to the second RSSI value, determining, by the server, that the first RSSI value exceeds the second RSSI value, and updating, by the server, a second database stored in the second memory device to set the first room as the location of the electronic bridge device.

In some embodiments, the method may further include steps of generating, by a temperature sensor coupled to the first beacon, temperature data, and sending, by the temperature sensor, the temperature data to the first beacon, the first beacon data including the temperature data and a temperature sensor beacon identifier.

In some embodiments, the temperature data may include ambient temperature values measured within a temperature-controlled device that is associated with the equipment identifier. The method may further include steps of referencing, by the server, the temperature sensor beacon identifier against a first database of the second memory device to identify the temperature-controlled device, the first database defining a plurality of associations between temperature sensor beacon identifiers and equipment including temperature-controlled devices, identifying, by the server, the temperature data of the first beacon data, updating, by the server, a second database of the second memory device to define the temperature data as being associated with the temperature-controlled device, determining, by the server based on the temperature data, that a predetermined threshold temperature value at the temperature-controlled devices has been exceeded, and causing, by the server, an alert to be sent to a user device, the alert indicating that the predetermined threshold temperature value has been exceeded.

In some embodiments, the method may further include a step of generating, with a diagnostic device, diagnostic data that includes measurements of one or more vital signs of a patient. The diagnostic device may be coupled to the first beacon. The first beacon may include a diagnostic beacon. The first beacon data may include diagnostic beacon data that includes the diagnostic data generated by the diagnostic device and that includes an equipment identifier associated with the diagnostic device.

In some embodiments, the method may further include steps of referencing, by the server, the equipment identifier against a first database of the second memory device to identify the diagnostic device, the first database defining a plurality of associations between equipment identifiers and equipment including diagnostic devices, identifying, by the server, a patient associated with the diagnostic device, identifying, by the server, the diagnostic data of the diagnostic beacon data, and updating, by the server, a second database of the second memory device to define the diagnostic data as being associated with both the diagnostic device and the patient.

In some embodiments, wirelessly broadcasting the first beacon signal may include wirelessly broadcasting the first beacon signal via a wireless personal area network. Broadcasting the second beacon signal may include broadcasting the second beacon signal via the wireless personal area network. Receiving the first beacon data and the second beacon data from the electronic bridge device may include receiving the first beacon data and the second beacon data from the electronic bridge device via a wide area network including the internet.

DETAILED DESCRIPTION

Figure 1:
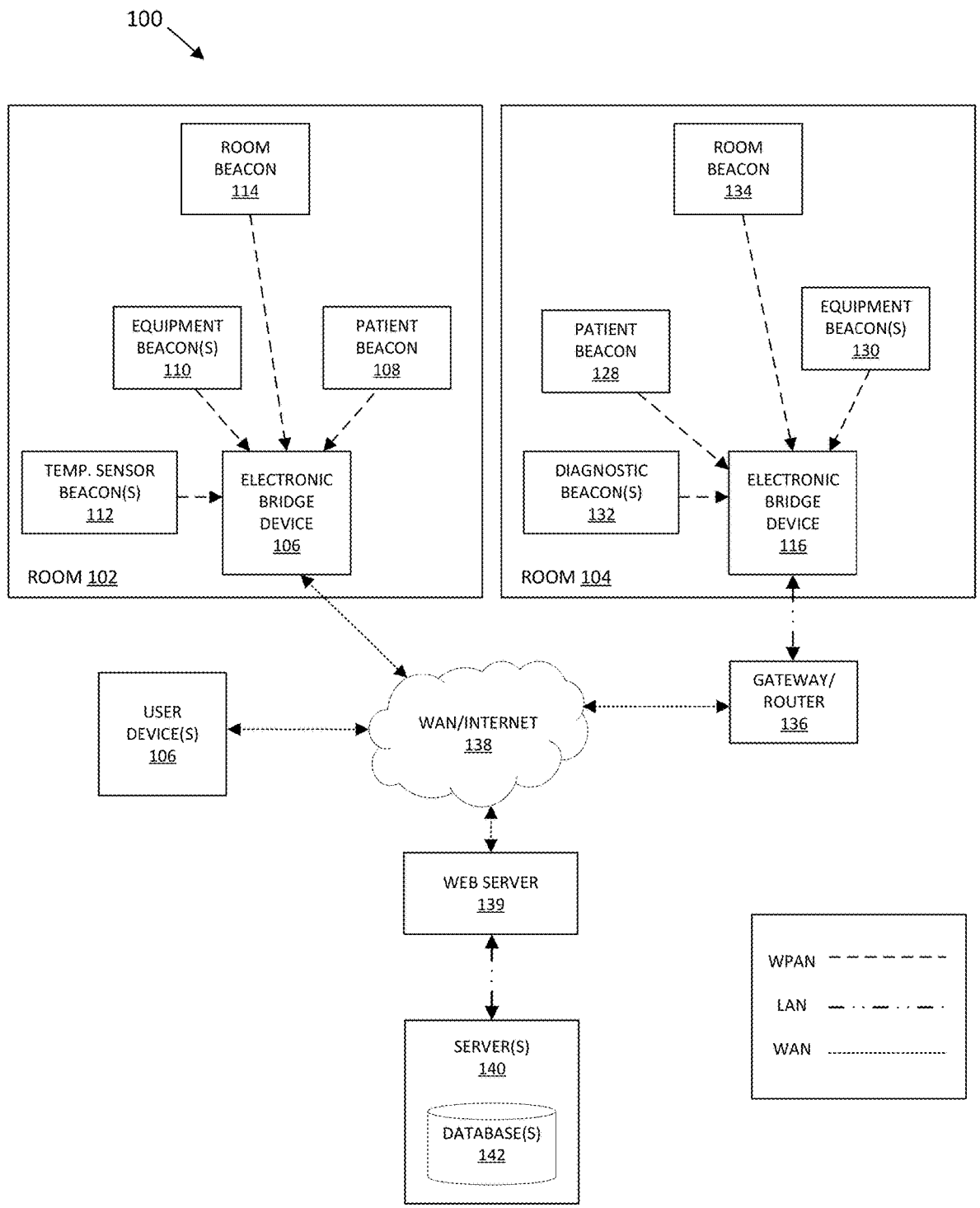
FIG. 1 shows an illustrative asset tracking system, in accordance with an embodiment.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

FIG. 1 shows an illustrative asset tracking system 100, which may use a combination of portable bridge devices and beacons (e.g., active radio-frequency identification (RFID) tags) to track the locations and/or other characteristic data of equipment or other assets (e.g., furniture, consumable goods, medicine, etc.), and/or people (e.g., doctors, nurses, and/or patients in hospital settings). The system 100 may include room beacons 114 and 134, equipment beacons 110 and 130, patient beacons 108 and 128, one or more diagnostic beacons 132, one or more temperature sensor beacons 112, electronic bridge devices 106, 116, a gateway or router 136, one or more servers 140, and a wide area network 138, such as the Internet. Here, different line styles are used to illustrate different types of connections between devices: Personal Area Network (PAN) connections (e.g., Bluetooth Low Energy), Local Area Network (LAN) connections (e.g., Ethernet, WiFi®), and Wide Area Network (WAN) connections (e.g., representing internet connections via ISPs and/or connections to the WAN or internet via a broadband wireless communication protocol such as 3G, 4G, 4G LTE, 5G, and the like). The term "electronic bridge devices", as used herein, may refer to mobile devices such as smartphones or tablets, laptops, special purpose internet-of-things (IoT) devices, non-portable desktop computers or workstations, wireless vital monitors that include at least a memory and a processor, and/or the like.

In the present example, two rooms, room 102 and room 104, are shown, each of which are shown to respectively contain multiple beacons and a portable bridge device. The rooms 102 and 104 may, for example, represent the rooms of two different patients within a hospital or other medical facility.

One or more user devices 106 may be connected to the servers 140 via the network 138 and the web server 139. The user devices 106 may include one or more mobile devices, laptops, personal computers, tablets, and/or other devices capable of sending information to and receiving information from the servers 140. As will be described, the user devices 106 may be configured to receive alerts from the servers 140 when data values monitored by the servers 140 exceed predetermined thresholds.

A web server 139 may be disposed between the network 138 and the servers 140, such that access to the servers 140 is controlled by the web server 139, and such that information/data sent by and received by the servers 140 is passed through and handled by the web server 139.

The room 102 may include an electronic bridge device 106, a patient beacon 108, one or more equipment beacons 110, one or more temperature sensor beacons 112, and a room beacon 114. The room 104 may include an electronic bridge device 116, a patient beacon 128, one or more equipment beacons 130, one or more diagnostic beacons 132, and a room beacon 134. Each of the beacons 108, 110, 112, 114, 128, 130, 132, and 134 may be an active RFID tag configured to periodically broadcast a beacon signal that includes beacon data. For example, the period between beacon signal broadcasts performed by a beacon may be between approximately 1 ms and 100 ms (e.g., 5 ms). The beacon data may be broadcast using a Bluetooth® wireless communication protocol, such as the Bluetooth Low Energy (BLE) wireless personal area network communication protocol. The information included in the beacon data may vary according to the particular beacon used to broadcast it, as will be described.

Each of the patient beacons 108 and 128 may be personal locating beacons that are incorporated into a wearable device (e.g., wristband, necklace, badge, and/or the like) worn by a corresponding patient. Beacon data (i.e., "patient beacon data") included in the beacon signals (i.e., "patient beacon signals") broadcast by each of the patient beacons 108 and 128 may include a patient identifier ("patient ID") which may be a unique sequence of characters that identifies a patient associated with that patient beacon. For example, the unique sequence of characters may be a Media Access Control (MAC) address of the patient beacon, and the MAC address may be associated with the patient in one or more of the databases 142. In some embodiments, secondary patient information may associated with a given patient in the databases 142, such as the patient's room number, contact information for the patient's doctor or emergency contacts, and/or medical information about the patient. This secondary information may be accessed after determining that the MAC address of the patient beacon corresponds to the given patient. In some embodiments, the patient beacons 108 and/or 128 may instead be personal locating beacons associated with non-patient individuals (e.g., doctors, nurses, other employees), and the beacon data included in the beacon signals broadcast by these beacons may include unique identifiers (e.g., MAC addresses) that may be referenced against the databases 142 to uniquely identify such individuals.

Each of the equipment beacons 110 and 130 may be attached to or disposed on or in any equipment (e.g., medical equipment such as EKG/ECG machines, sterilizers, patient monitors, anesthesia machines, defibrillators, infusion pumps, medical ventilators, dialysis machines, incubators, cardiopulmonary bypass devices, pumps for the delivery of medicine, and/or the like), furniture (e.g., hospital beds, chairs, tables and/or the like), or other assets (e.g., containers of consumable materials such as medications and/or IV bags, wheelchairs, stretchers, IV poles, crash carts, and/or the like) disposed in room 102 or room 104, respectively. Beacon data (i.e., "equipment beacon data") included in the beacon signals (i.e., "equipment beacon signals") broadcast by each of the equipment beacons may include an equipment identifier ("equipment ID") which may be a sequence of characters that uniquely identifies a piece of equipment associated with that equipment beacon. For example, the unique sequence of characters may be a MAC address of the equipment beacon, and the MAC address may be associated with the corresponding device in one or more of the databases 142. In some embodiments, an equipment database of the databases 412 may maintain, for each of a number of assets/devices, one or more respective tables. For example, a given table of the equipment database may store the most recently determined location of a corresponding asset/device in association with a name of that device and/or a device ID. In some embodiments, the given table may store a historical record of locations at which the asset/device was previously determined to have been disposed. Secondary information, such as device type, expected location, and/or the like corresponding to a given device may be stored in one or more of the databases 142, in some embodiments, such that after resolving the association between an equipment beacon MAC address and a device, the secondary information about the device may be identified and retrieved from such a database. In some embodiments, the equipment beacons 110 and 130 may additionally provide device health information in the equipment beacon data, which may be stored in a table of the equipment database. For example, the device health information can include indications of whether a corresponding device is at risk of failure (e.g., unexpected shutdown), whether a lead wire of the corresponding device is broken, and/or whether repair or recalibration of the corresponding device is needed.

In some embodiments, the server(s) 140 may monitor the location of one or more assets/devices stored in the equipment database, and if the server(s) 140 determine that a given asset or device is in a location considered to be disallowed or unexpected for that asset or device, an alert may be triggered, which may cause a corresponding notification to be sent to one or more user devices, such as user device(s) 106. For example, such a notification may inform the recipient that a device is in a disallowed or unexpected location (e.g., one or more lists of disallowed or unexpected locations may be defined for the device in the equipment database or another of the databases 142), and may request confirmation of an action that has been taken by the recipient to resolve the alert. For example, such confirmation may be sent by a user device 106 to the server(s) 140 via the network 138 and the web server 139.

For example, a device such as a tablet computing device may be coupled to an equipment beacon such as equipment beacons 110, 130. The location of the tablet computing device may be tracked by the server(s) 140 based on at least equipment beacon data generated by the equipment beacon, as described herein. The server(s) 140 may periodically analyze the location of the tablet computing device. If the server(s) 140 determine that the tablet computing device is in a disallowed or unexpected location (e.g., outside of a room to which the tablet computing device has been assigned), a corresponding alert may be generated and sent to one or more of the user devices 106.

Each of the temperature sensor beacons 112 may be coupled to or integrated with a corresponding temperature sensor (e.g., that is disposed in room 102 in the present example). A given temperature sensor that is coupled to a given temperature sensor beacon 112 may be associated with a device (e.g., a refrigeration device), and may measure a temperature (e.g., an interior temperature within a refrigeration chamber of the refrigeration device) of that device. The temperature sensor may generate temperature data that includes measured temperatures and corresponding timestamps and may pass the temperature data to the given temperature sensor beacon 112 that is coupled to that temperature sensor. The given temperature sensor beacon 112 may then broadcast a beacon signal (i.e., "temperature sensor beacon signal) that includes beacon data (i.e., "temperature sensor beacon data") for the temperature sensor beacon 112. The temperature sensor beacon data may include a temperature sensor beacon ID (e.g., MAC address) that identifies the temperature sensor beacon 112. The temperature sensor beacon data may include the temperature data generated by the given temperature sensor. In some embodiments, the temperature sensor beacon data may include temperature data that was generated during the time period following the most recent broadcast performed by the temperature sensor beacon 112. In some embodiments, the temperature sensor or the temperature sensor beacons 112 may include an electronic buffer in which temperature data may be stored between broadcasts of the temperature sensor beacon signal.

The temperature sensor beacon data may be sent to the servers 140 by the electronic bridge device 106 via the network 138 and the web server 139. An illustrative temperature database of the databases 142 may include a table of temperature values that were measured by a temperature sensor coupled to the temperature sensor beacon 112. Each entry in the table may include a timestamp representing the time at which the temperature value was measured and/or a timestamp representing the time at which the corresponding temperature data was transmitted by the temperature sensor beacon 112. In some embodiments, each entry may also include a location of the temperature sensor beacon, which may correspond to a location of the bridge device (e.g., electronic bridge device 106) that received and routed the temperature sensor beacon data to the servers 140. An equipment ID or other identifying information corresponding to a device associated with the temperature sensor coupled to the temperature sensor beacon 112 may be stored in the temperature database in association with the tables of measured temperature data. In some embodiments, the temperature database may also include a separate table (i.e., a "current temperature table") that stores a "current" temperature value, which may be the temperature value most recently measured by the temperature sensor, or an average of the last predetermined number of temperature values most recently measured by the temperature sensor, as represented in the most recently received temperature sensor beacon data.

In some embodiments, the server(s) 140 may monitor the temperature data stored in the temperature database, and if the server(s) 140 determine that the temperature measured by a given temperature sensor is consecutively higher or lower than one or more predetermined thresholds for longer than a predefined period of time, an alert may be triggered, which may cause a corresponding notification to be sent to one or more user devices, such as user device(s) 106. For example, such a notification may inform the recipient of the temperature threshold that has been exceeded, and may request confirmation of an action that has been taken by the recipient to resolve the alert. For example, such confirmation may be sent by a user device 106 to the server(s) 140 via the network 138 and the web server 139.

While temperature sensors and temperature sensor beacons are discussed in the present example, it should be understood that other sensor types and corresponding sensor beacons may be implemented in a similar way, such that sensor data (e.g., light sensor data, humidity sensor data, G-force/acceleration sensor data, and/or the like) may be collected, transmitted and stored in a corresponding database of the databases 142, and/or may be monitored by the server(s) 140.

Each of the diagnostic beacons 132 may be coupled to or integrated with a corresponding diagnostic device (e.g., that is disposed in room 104 in the present example). For example, a given diagnostic device may be configured to measure one or more items of diagnostic information (e.g., EKG/ECG readings, and/or vital signs such as heart rate, body temperature, blood pressure, respiratory rate, and/or the like; sometimes referred to herein as "diagnostic data") of a patient. The diagnostic device may include one or more temperature sensors, pressure sensors, fibre-optic breath rate sensors, pulse oximeters, accelerometers, EKG/ECG electrodes, and/or the like, which may be used to generate the diagnostic information. The diagnostic device may periodically pass the diagnostic information to the given diagnostic beacon 132 to be included in the beacon data (i.e., "diagnostic beacon data") to be included in the next beacon signal (i.e., "diagnostic beacon signal") broadcast by the given diagnostic beacon 132. The diagnostic beacon 132 receives the diagnostic information, and broadcasts a diagnostic beacon signal that includes the diagnostic information in its diagnostic beacon data. In some embodiments, the diagnostic beacon data may only include diagnostic information that was generated during the time period following the most recent broadcast performed by the diagnostic beacon 132. In some embodiments, the diagnostic beacon and/or the diagnostic device may include an electronic buffer in which diagnostic data may be stored between diagnostic beacon signal broadcasts. In some embodiments, diagnostic devices that include or that are coupled to the diagnostic beacons 132 may be leadless/wireless, and may transmit diagnostic data solely via the diagnostic beacons 132. Such leadless patient monitoring may be advantageous compared to conventional lead-based patient monitoring in that it tends to be less obtrusive and allows for greater freedom of movement by the patient.

Diagnostic beacon data may be transmitted to the servers 140 by the electronic bridge device 106 via the network 138 and the web server 139, and may be stored in a corresponding database of the databases 142. For example, a diagnostic database may be included in the databases 142, which may include a table of diagnostic information that was measured by a diagnostic device coupled to the diagnostic beacon 132. Each entry in the table may include a given diagnostic value of the diagnostic information and a timestamp representing the time at which the given diagnostic value was measured and/or a timestamp representing the time at which the corresponding diagnostic beacon data was transmitted by the diagnostic beacon 132. Each entry may also define a diagnostic data type (e.g., EKG/ECG reading, heart rate, body temperature, blood pressure, respiratory rate, and/or the like) corresponding to the type of diagnostic information represented by the given diagnostic value. In some embodiments, each entry may also include a location of the diagnostic beacon 132, which may correspond to a location of the bridge device (e.g., electronic bridge device 116) that received and routed the diagnostic beacon data to the servers 140. An equipment ID or other identifying information corresponding to the diagnostic device associated with the diagnostic beacon 132 may be stored in the diagnostic database in association with the table(s) of measured diagnostic data. In some embodiments, the diagnostic database may also include one or more separate tables ("current diagnostic value tables") that stores a "current" diagnostic information value for each measured diagnostic data type measured by the corresponding diagnostic device. In each of the current diagnostic value tables, the current diagnostic information value may represent a most recently measured diagnostic value of the corresponding diagnostic data type, or an average of the last predetermined number of the most recently measured diagnostic values of the diagnostic data type, as represented in the most recently received diagnostic beacon data.

In some embodiments, the server(s) 140 may monitor the diagnostic information stored in the temperature database, and if the server(s) 140 determine that diagnostic values of a given diagnostic data type are consecutively higher or lower than one or more predetermined thresholds for longer than a predefined period of time, an alert may be triggered, which may cause a corresponding notification to be sent to one or more user devices, such as user device(s) 106. For example, such a notification may inform the recipient of the threshold that has been exceeded and the corresponding diagnostic data type, and may request confirmation of an action that has been taken by the recipient to resolve the alert. For example, such confirmation may be sent by a user device 106 to the server(s) 140 via the network 138 and the web server 139.

The room beacons 114 and 134 may periodically broadcast respective beacon signals (i.e., "room beacon signals"). Each room beacon signal includes a room identifier ("room ID") which may be a unique sequence of characters that uniquely identifies a room associated with the room beacon that generated the room beacon signal. For example, the sequence of characters may be a MAC address of the room beacon. For example, the room ID included in the room beacon signals broadcast by the room beacon 114 identifies room 102, whereas the room ID included in the room beacon signals broadcast by the room beacon 134 identifies room 104. A portable bridge device, such as the mobile device 106 or the laptop 116, may wirelessly receive one or multiple room beacon signals using a PAN communication protocol, such as BLE, and may estimate its own location based on the room beacon signal having the highest received signal strength (e.g., based on relative signal strength index (RSSI) measurements of each received room beacon signal) and the room ID included in that room beacon signal. As will be described, for embodiments in which a given electronic bridge device is portable, the server 140 may estimate the locations of assets and people associated with other beacon signals received by the electronic bridge device based on the room ID included in the room beacon signal having the highest received signal strength, as measured by the electronic bridge device.

For embodiments in which the electronic bridge device 106 is a mobile device such as a smart phone, tablet, or another wireless-broadband-enabled device, the electronic bridge device 106 device may wirelessly receive beacon signals broadcast by the patient beacon 108, the equipment beacon(s) 110, the temperature sensor beacon(s) 112, and the room beacon 112 using a PAN communication protocol, such as BLE. The electronic bridge device 106 may store beacon data included in the beacon signals received from these devices in one or more local memory devices. The electronic bridge device 106 may periodically send the beacon data and/or information derived from the beacon data to one or more servers 140 via the WAN/internet 138. For example, the electronic bridge device 106 may be wirelessly connected to the WAN/internet 138 using a wireless broadband protocol, such as 4G, 4G LTE, or 5G, and may transmit beacon data via this connection. When sending beacon data to the server(s) 140, the electronic bridge device 106 may also provide a bridge identifier ("bridge ID") which may be a unique sequence of characters (e.g., a MAC address of the electronic bridge device) that uniquely identifies the electronic bridge device 106.

For embodiments in which the electronic bridge device 116 is a computer device (e.g., laptop, non-portable desktop computer, workstation, and/or the like) that is capable of wireless and, optionally, wired electronic communication, the electronic bridge device 116 may wirelessly receive beacon signals broadcast by the patient beacon 128, the equipment beacon(s) 130, the diagnostic beacon(s) 132, and the room beacon 134 using a PAN communication protocol, such as BLE. The electronic bridge device 116 may store beacon data included in the beacon signals received from these devices in one or more local memory devices. The electronic bridge device 116 may periodically send the beacon data and/or information derived from the beacon data to the one or more servers 140 via the WAN/internet 138 and a gateway or router 136. For example, the electronic bridge device 116 may be wirelessly connected to the gateway or router 136 that is connected to the WAN/internet 138 via the network of an internet service provider (ISP). The electronic bridge device 116 may communicate with the gateway or router 136 using a wireless communication protocol, such as WiFi® as part of a LAN. When sending beacon data to the server(s) 140, the electronic bridge device 116 may also provide a bridge identifier ("bridge ID") which may be a sequence of characters (e.g., MAC address) that uniquely identifies the electronic bridge device 116.

The servers 140 may receive beacon data and/or information derived from beacon data from the mobile device 106, the laptop 116, and other portable bridge devices. The servers 140 may include one or more databases 142, which may be stored on one or more memory devices of the servers 140. Entries in the database(s) 142 may include subsets (e.g., tables) of beacon data and corresponding time stamps.

In some embodiments, the servers 140 may be configured to, in response to a query from another computer device (e.g., received via the WAN/internet 138), determine, based on the beacon data stored in the database(s) 142, the location of the equipment or patient (e.g., based on either an equipment name or a patient name identified in the query, or based on a given equipment ID, patient ID, or bridge ID identified in the query), and may send the determined location to the computer device that sent the query.

Figure 2:
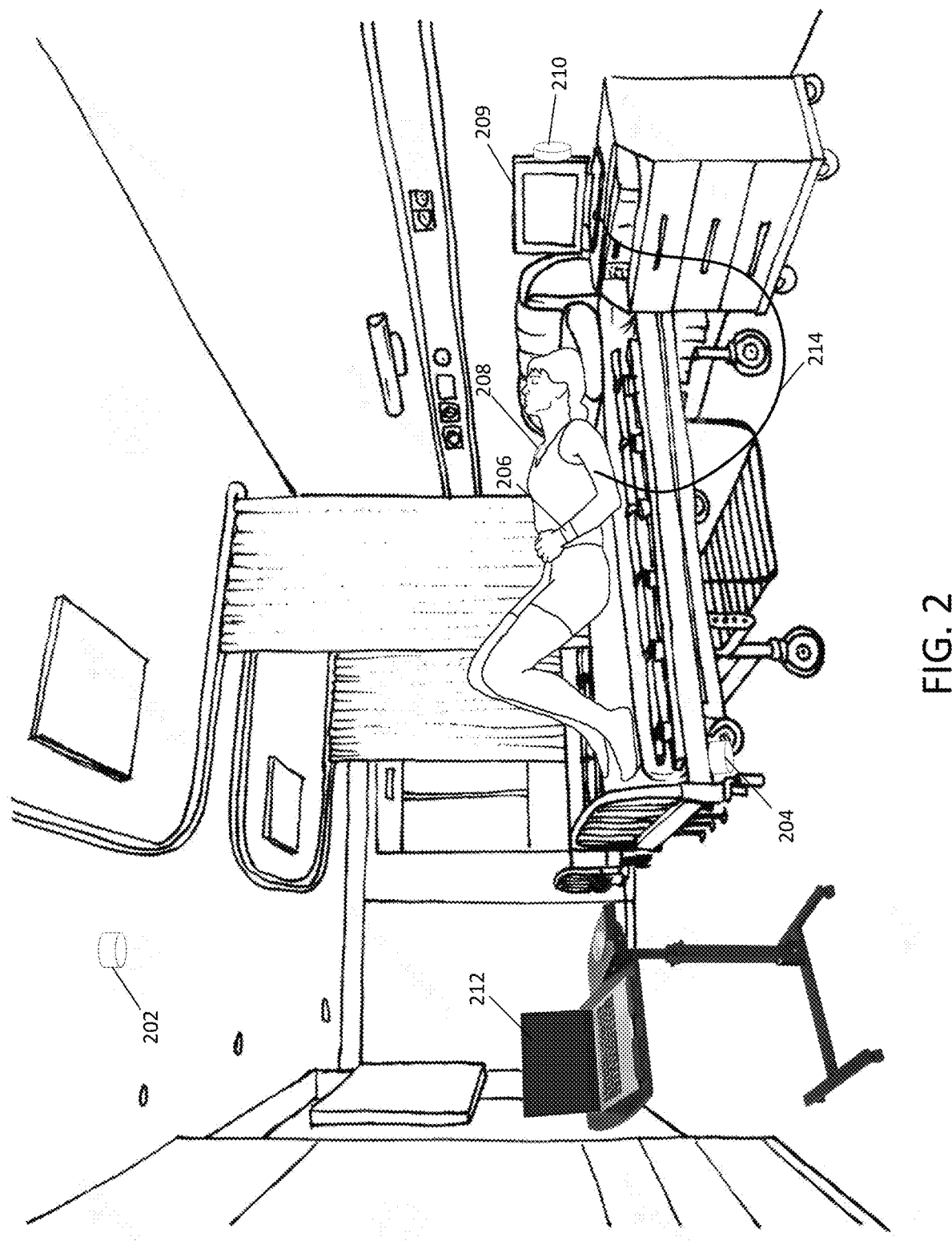
FIG. 2 shows an illustrative implementation of a portion of an asset tracking system within a room, in accordance with an embodiment.

FIG. 2 shows an illustrative room setting in which a tracking system, such as the tracking system 100 of FIG. 1, is employed. As shown, the room may include beacons 202, 204, 206, 208, and 210, a medical device 209, and a laptop computer 210.

The beacon 202 may be a room beacon (e.g., room beacon 114, 134, FIG. 1) that periodically broadcasts a beacon signal that includes a room ID. The room ID may, for example, be a MAC address of the beacon 202. The room ID may be associated with the location of the room in a database of a back-end server (e.g., databases 142 of servers 140 of FIG. 1) that is coupled to the laptop 212, such that the location can be determined by referencing (e.g., with a processor of the server) the room ID against the database. While the beacon 202 is shown here to be disposed on the room's ceiling, it should be understood that the beacon 202 could instead be disposed on other surfaces within the room (e.g., wall, floor, door, electrical outlet, or other applicable surfaces).

The beacon 204 may be an equipment beacon (e.g., equipment beacons 110, 130, FIG. 1), shown here to be attached to a hospital bed. The beacon 204 may periodically broadcast an equipment beacon signal that includes an equipment ID (e.g., a MAC address of the beacon 204) associated with the hospital bed (e.g., in a database entry of a database of the back-end server). The laptop 212 or the back-end server may determine a location of the laptop 212 by determining that the room beacon signal that the laptop 212 receives from the beacon 202 is stronger (e.g., has a higher RSSI) than any other room beacon signal received by the laptop 212. Once the location of the laptop 212 is determined in this way, and the laptop receives the equipment beacon signal from the beacon 204, the laptop may send the equipment beacon data contained in the equipment beacon signal to the back-end server, which may create a database entry that associates the hospital bed associated with the beacon 204 to the location of the laptop 212 (i.e., to the location of the room). For example, the back-end server may reference the equipment ID against a first database identify that the hospital bed is associated with the equipment ID, and may then create a corresponding database entry in a second database (e.g., equipment database) that associates the identified hospital bed with the location of the laptop 212 (i.e., the location of the room). In some embodiments, such database(s) may maintain historical records of equipment ID locations for the hospital bed associated with the beacon 204. A person or automated system accessing the database may determine, based on the created database entry, the likely location of the hospital bed as being the room corresponding to the location that is associated with the equipment ID of the hospital bed.

The beacon 206 may be a patient beacon (e.g., patient beacons 108, 128, FIG. 1), shown here to be included in a wristband worn by a patient. The beacon 206 may periodically broadcast a patient beacon signal that includes a patient ID (e.g., which may be a MAC address of the patient beacon) that is associated with the patient wearing the wristband (e.g., such association being defined in a database of the back-end server). The laptop 212 may receive the patient beacon signal from the beacon 206 and may forward the patient beacon data contained therein to the back-end server. After the location of the laptop has been determined based on the room beacon signal, as discussed above, the back-end server may receive the patient beacon data and create a database entry in a corresponding database of the back-end server. For example, the back-end server may reference the patient ID against a first database to identify the patient associated with the patient ID, and may then create a database entry in a second database (e.g., a patient database) that associates the identified patient with the most recently determined location of the laptop 212. In this way, a person or automated system accessing the database may determine, based on the created database entry, the likely location of the patient as being the room corresponding to the room ID that is associated with the patient ID of the patient.

The beacon 208 may be a leadless diagnostic beacon (e.g., diagnostic beacon 132, FIG. 1), shown here to be attached to the torso of the patient. The beacon 208 may periodically broadcast a diagnostic beacon signal that includes diagnostic beacon data, which may include diagnostic information associated with the patient. The beacon 208 may be integrated with a diagnostic device, such as a temperature sensor, a blood pressure monitor, a heart rate monitor, an EKG/ECG electrode, and/or the like, such that measurements (e.g., of body temperature, blood pressure, heart rate, EKG/ECG readings, and/or other applicable measurements) made by the diagnostic device may be used to generate the diagnostic information that is included in the diagnostic beacon broadcast by the beacon 208. The laptop 212 may receive the diagnostic beacon signal from the beacon 208 and may forward the diagnostic beacon data contained therein to the back-end server. After the location of the laptop 212 has been determined based on the room beacon signal, as discussed above, the back-end server may receive the diagnostic beacon data from the laptop 212 and create a database entry in a corresponding database of the back-end server. In some embodiments, the patient ID output by the patient beacon 206 may be used by the back-end server to identify the patient to whom the diagnostic information corresponds. In other embodiments, an diagnostic device ID (e.g., MAC address) of the diagnostic beacon itself may be included in the diagnostic beacon data, and may be associated with the patient in a database of the back-end server, such that the back-end server may reference the diagnostic device ID against the database to identify the patient. The back-end server may identify the patient associated with the diagnostic beacon data, via a method described above, and may then create a database entry or series of database entries in one or more tables of a diagnostic database. The created entries may associates the diagnostic information stored in the database entries with the identified patient. In some embodiments, a patient record associated with the patient ID may be updated to include the diagnostic information in response to the association of the identified patient with the diagnostic information. In this way, a person or automated system may access the diagnostic information via the database and may determine the patient to whom the diagnostic information corresponds.

The beacon 210 may act as both an equipment beacon (e.g., equipment beacons 110, 130, FIG. 1) and a diagnostic beacon (e.g., diagnostic beacons 132, FIG. 1), shown here to be attached to a medical device 209 that is coupled to the patient via one or more leads 214, and that is configured to generate diagnostic information for the patient. It should be understood that one or more devices (e.g., sensors, IV needles, a ventilator mask, or the like; not shown) may be disposed at a distal end of the lead(s) 214 that is connected to the patient. It should be understood that a simplified depiction of the medical device 209 is provided here, and that the medical device 209 may correspond to one of a number of different pieces of medical equipment. For example, the medical device 209 may be an EKG machine configured to generate EKG data for the patient, a vital signs monitor configured to generate vital signs data (e.g., pulse, pulse oximetry, blood pressure, respiration rate, body temperature, EKG/ECG readings, and/or other applicable vital signs) based on measurements taken from the patient by the vital signs monitor, a computerized pump for delivery of medicine to the patient, a ventilator, and/or the like. The diagnostic information may be organized temporally (i.e., with data points being ordered according to the time at which they were measured). The beacon 210 may receive the diagnostic information from the medical device 209, and may periodically broadcast a diagnostic beacon signal that includes the diagnostic information and an equipment ID (e.g., a MAC address of the beacon 210), which may be associated with the medical device 209 in a database of the back-end server. The laptop 212 may receive the diagnostic beacon signal from the beacon 208 and may forward the diagnostic beacon data contained therein to the back-end server. After the location of the laptop 212 has been determined based on the room beacon signal, as discussed above, the back-end server may receive the diagnostic beacon data from the laptop 212 and create one or several database entries in a corresponding database of the back-end server. As discussed above, the back-end server may determine an association between the patient and the diagnostic information included in the diagnostic beacon data via reference to a database that stores such associations, and the back-end server may further determine an association between the medical device 209 and the equipment ID via reference to another database that stores such associations. The diagnostic database entries corresponding to the diagnostic information may be associated with the patient, the medical device 209, and/or the location of the laptop 212 (i.e., the room). In some embodiments, a patient record associated with the patient may be updated to include the diagnostic information responsive to the creation of the diagnostic database entries.

The laptop 212 may communicate with the beacons 202, 204, 206, 208, and 210 using a wireless communication protocol such as that defined by IEEE 802.15 (e.g., WPAN; Bluetooth®/BLE). The laptop 212 may communicate with one or more remote servers (e.g., server 140, FIG. 1) via a different wireless communication protocol, such as IEEE 802.11 (e.g., WLAN; WiFi®).

Figure 3:
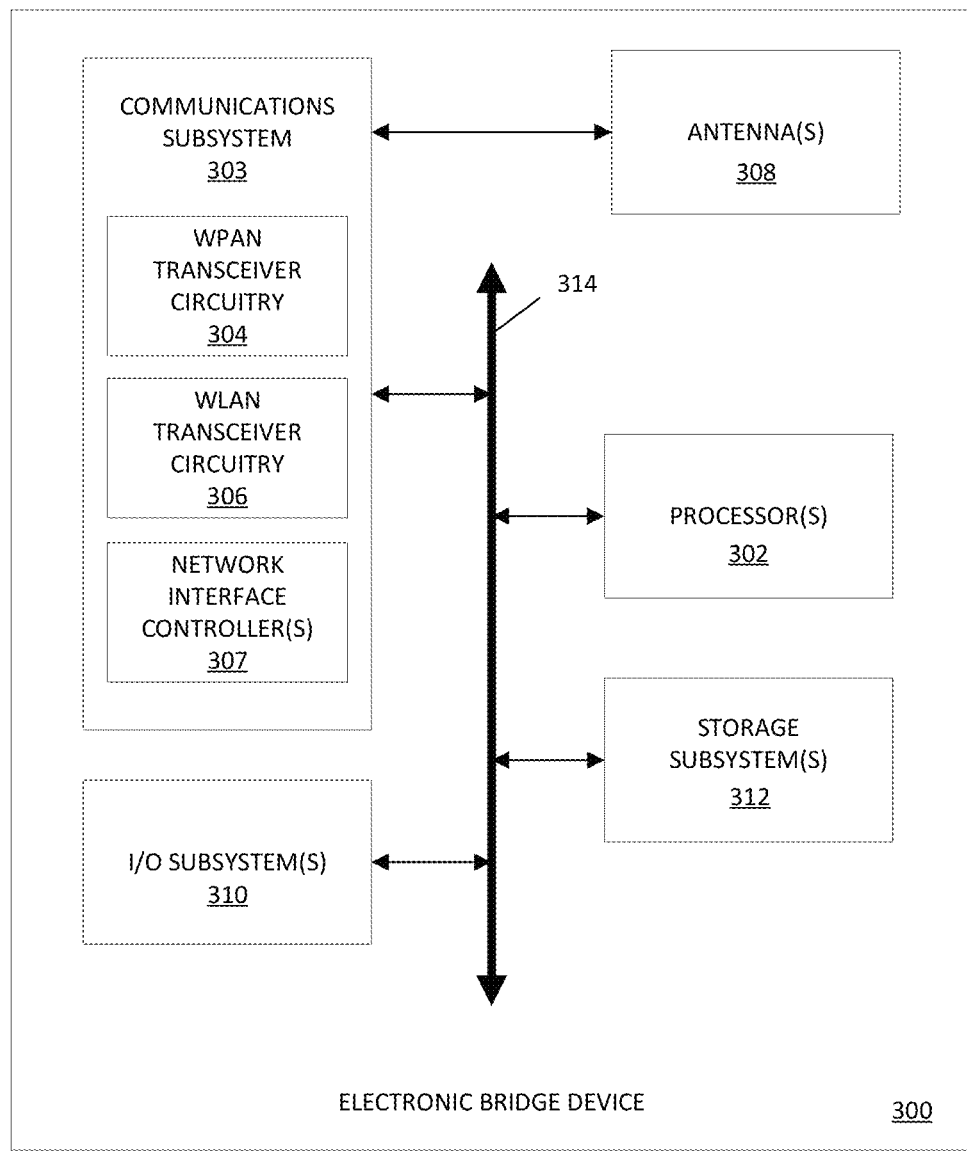
FIG. 3 shows an illustrative electronic bridge device that may be included in the asset tracking system of FIG. 1.

FIG. 3 shows an illustrative electronic bridge device 300, which may correspond to any of the electronic bridge devices 106, 116 of FIG. 1, and the laptop 212 of FIG. 2 in some embodiments. In this example, the device 300 includes one or more processors 302, a communications subsystem 303, one or more antennas 308, an input/output (I/O) subsystem 310, one or more storage subsystems 312, and a bus subsystem 314. The communications subsystem may be coupled to the bus subsystem 314 and the antennas 308, and may include WPAN transceiver circuitry 304, WLAN transceiver circuitry 306, and one or more network interface controllers 307. In some embodiments, the device 300 may include wired Ethernet network communication circuitry (e.g., in the form of an Ethernet network interface card) in place of or in addition to the WLAN transceiver circuitry 306.

The bus subsystem 314 provides a mechanism for letting the various components and subsystems of device 300 communicate with each other. Although the bus subsystem 314 is shown here as a single bus, alternative embodiments of the bus subsystem may utilize multiple buses. The bus subsystem 314 may be any of several types of bus structures including a memory bus or memory controller, a peripheral bus, and a local bus using any of a variety of bus architectures. Such architectures may include, for example, an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard, for example.

The processor(s) 302, which may be implemented as one or more integrated circuits (e.g., a conventional processor, microprocessor, or microcontroller), controls the operation of device 300. The processor(s) 302 may include one or multiple processors, such as single core and/or multicore processors. The processor(s) 302 may execute a variety of software processes embodied in program code, and may maintain multiple concurrently executing programs or processes. At any given time, some or all of the program code to be executed can reside in processor(s) 302 and/or in storage subsystem 312. In some embodiments, device 300 may include one or more specialized processors, such as digital signal processors (DSPs), outboard processors, graphics processors, application-specific processors, and/or the like.

The I/O subsystem 310 may include device controllers for one or more user interface input devices and/or user interface output devices. User interface input and output devices may be integral with the device 300 (e.g., integrated audio/video systems, and/or touchscreen displays), or may be separate peripheral devices which are attachable/detachable to/from the device 300. The I/O subsystem 310 may provide one or several outputs to a user by converting one or several electrical signals to the user in perceptible and/or interpretable form (e.g., audible/visible), and may receive one or several inputs from the user by generating one or several electrical signals based on one or several user-caused interactions with the I/O subsystem such as the depressing of a key or button, the moving of a mouse, the interaction with a touchscreen or trackpad, the interaction of a sound wave with a microphone, or the like.

The storage subsystems 312 may include hardware and software components used for storing data and program instructions, such as system memory and/or a computer-readable storage media. The system memory and/or computer-readable storage media may store program instructions that are loadable and executable on the processor(s) 302, as well as data generated during the execution of these programs.

The storage subsystems 312 also may provide one or more tangible computer-readable storage media for storing the basic programming and data constructs that provide the functionality of some embodiments. Software (e.g., programs, code modules, instructions) that, when executed by a processor, provide the functionality described herein may be stored in storage subsystems 312. These software modules or instructions may be executed by the processor(s) 302. The storage subsystems 312 may also store one or more databases that define associations between various data elements, data arrays, and/or data objects, which may include patient IDs, equipment IDs, room IDs, sensor data, diagnostic information, and/or device health information.

The communication subsystem 303 may provide a communication interface between the device 300 and external computing devices (e.g., external servers and/or beacons) via one or more communication networks, which may include LANs, WANs (e.g., the internet), and PANs.

The network interface controllers 307 may include one or more Ethernet cards, as well as wireless network interface controllers, wireless network adapters, and the like.

The WLAN transceiver circuitry 306 may include radio frequency (RF) transceiver components for sending and receiving data wirelessly according to the IEEE 802.11 family standards (e.g., WiFi®).

The WPAN transceiver circuitry 304 may include RF transceiver components for sending and receiving data wirelessly according to the IEEE 802.15 family standards (e.g., Bluetooth®, BLE).

The antennas 308 may be coupled to the WPAN transceiver circuitry 304 and the WLAN transceiver circuitry 306 of the communication subsystem 303. In some embodiments, a single antenna 308 may be used to send and receive signals using both the WPAN transceiver circuitry 304 and the WLAN transceiver circuitry. In other embodiments, a first antenna of the antennas 308 may be dedicated to handling WLAN communications that are sent and received by the WLAN transceiver circuitry 306, while a second antenna of the antennas 308 may be dedicated to handling WPAN communications that are sent and received by the WPAN transceiver circuitry 304.

Figure 4:
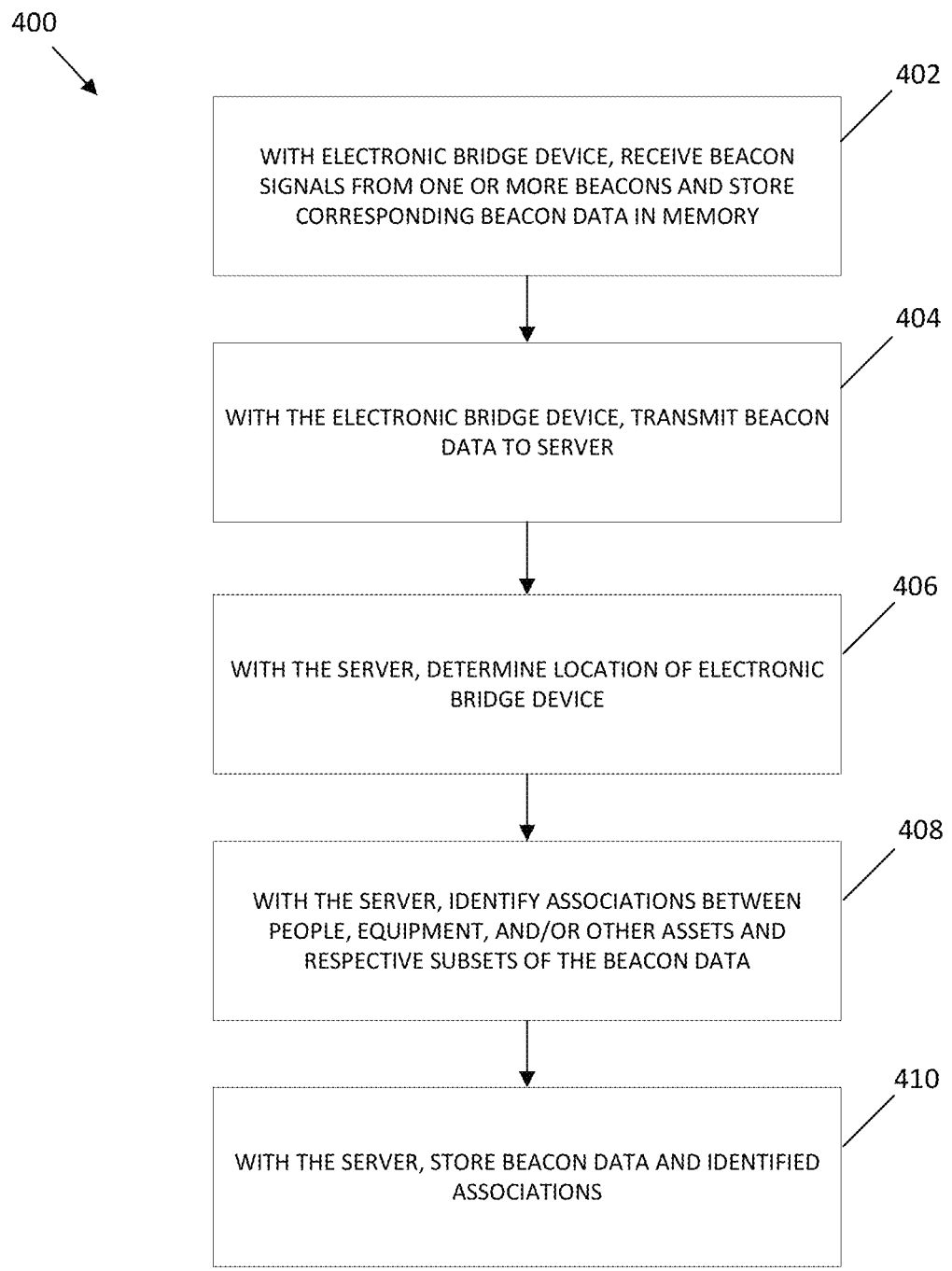
FIG. 4 shows an illustrative process flow for a method by which characteristic data may be collected by an electronic bridge device of an asset tracking system, in accordance with an embodiment.

FIG. 4 shows an illustrative process flow of a method 400 by which data ("beacon data") may be collected from beacons (e.g., beacons 108, 110, 112, 114, 128, 130, 132, 134, 202, 204, 206, 208, 210, FIGS. 1, 2) by an electronic bridge device (e.g., electronic bridge device 106, 116, laptop 212, FIGS. 1, 2), and may be sent to, analyzed, processed, and stored by a server (e.g., servers 140, FIG. 1). The method 400 may, for example be performed via the execution of computer-readable instructions via one or more computer processors (e.g., processors 302, FIG. 3), which may be included in one or more computer servers (e.g., server 140, FIG. 1). The steps of the method 400 are described as being performed using one such processor, though it should be understood that multiple processors may be used.

At step 402, the electronic bridge device receives beacon signals from one or more beacons, and stores corresponding beacon data in memory. For example, the beacons may include room beacons, equipment beacons, diagnostic beacons, temperature sensor beacons, and/or patient beacons. The beacon signals may collectively include a set of "beacon data," which may be organized into "subsets" where each subset of beacon data corresponds to a respectively unique source beacon. For example, room beacon signals may include room beacon data including respective room IDs, equipment beacon signals may include equipment beacon data including respective equipment IDs and/or device health information, diagnostic beacon signals may include diagnostic beacon data defining diagnostic information and optionally equipment IDs, temperature sensor beacons may include temperature sensor beacon data including temperature data and temperature sensor beacon IDs, and patient beacon signals may include patient beacon data including respective patient IDs. For example, the electronic bridge device may receive the beacon signals via one or several WPAN connections (e.g., Bluetooth®/BLE).

At step 404, the electronic bridge device transmits the beacon data to one or more computer servers (e.g., server 140, FIG. 1; referred to henceforth as "the server"). For example, the electronic bridge device may transmit the data to the server(s) via a wireless connection to a LAN and/or via a WAN or the internet. For example, the electronic bridge device may transmit beacon data that has been collected since the bridge device's last transmission to the server at a predefined regular interval.

At step 406, the server determines a location of the electronic bridge device. In some embodiments, the electronic bridge device may have a static location that is known by (e.g., stored in a memory device of) the server. In some embodiments, the static location of the electronic bridge device may be represented as a room ID corresponding to the room in which the electronic bridge device is known to be located. In other such embodiments, the static location of the electronic bridge device may not be associated with a particular room, but may be associated with another feature of the facility (e.g., a nurse's station).

Figure 6:
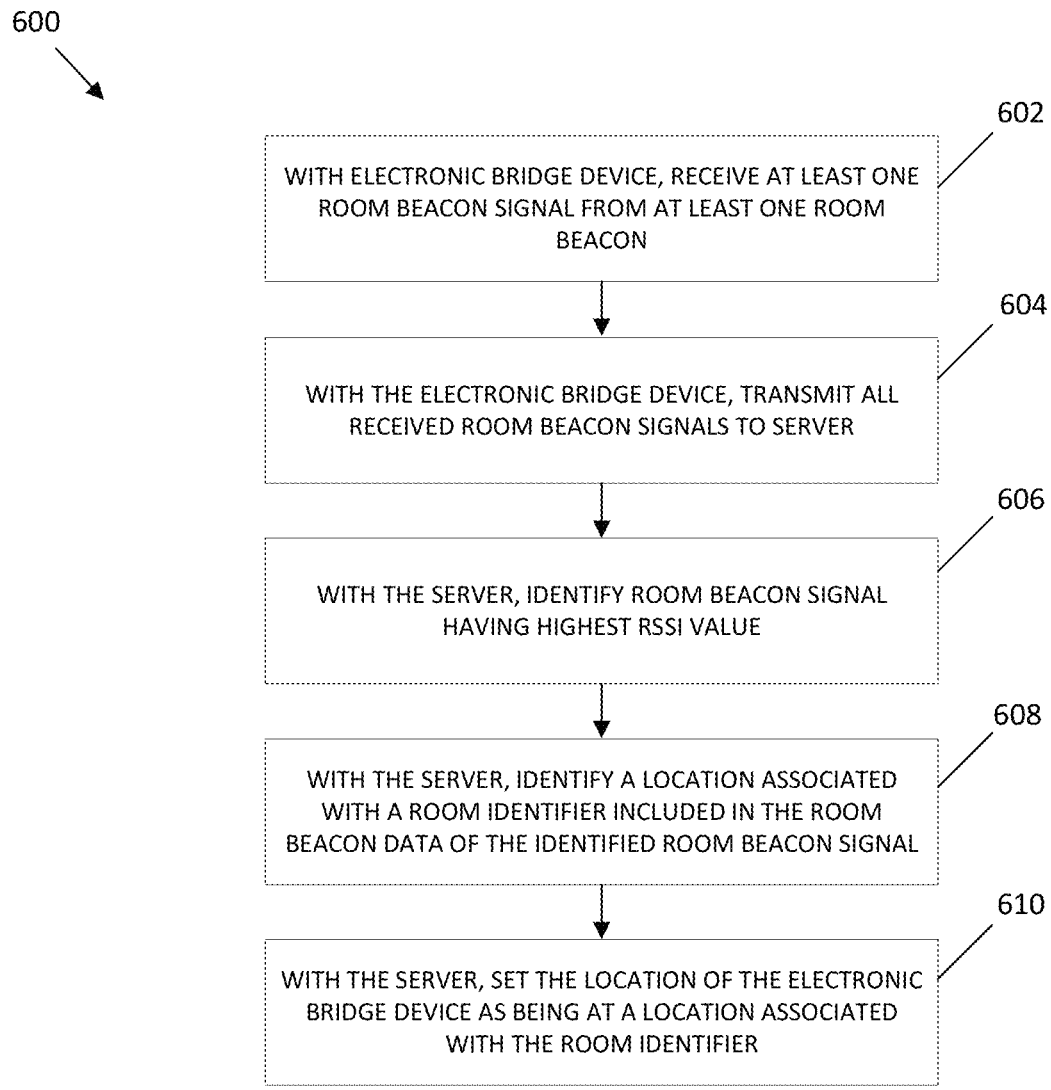
FIG. 6 shows an illustrative process flow for a method by which characteristic data may be collected by an electronic bridge device of an asset tracking system, in accordance with an embodiment.

In some alternate embodiments, the electronic bridge device may be portable (e.g., a smartphone, tablet, laptop, and/or the like), and the location of the electronic bridge device may be determined (e.g., approximated) based on a room beacon signal received by the electronic bridge device (e.g., according to the method 600 of FIG. 6). For example, the server may determine that the location of the electronic bridge device is the room associated with the room ID included in the room beacon data included in the room beacon signal having the highest received signal strength indicator (RSSI) among room beacon signals received by the electronic bridge device.

At step 408, the server analyzes the beacon data and identifies associations between people (e.g., patients), equipment, measurement data (e.g., temperature data, diagnostic data, and/or other sensor data), and/or locations represented in the subsets of the beacon data. For example, the server may access a look-up table or other database stored in a memory of the server, which may define associations between patients and/or equipment and various patient IDs, equipment IDs, temperature sensor beacon IDs, and/or other identifiers that may be included in the subsets of beacon data. The server may then reference the patient IDs and/or equipment IDs included in the subsets of beacon data against the database to determine which patients, rooms and/or equipment correspond to the patient IDs, equipment IDs, temperature sensor beacon IDs, and/or other identifiers. The server may then define associations between the identified equipment and patients and measurement data and/or locations included in the subsets of beacon data. For example, the server may determine that a set of diagnostic beacon data and a set of patient beacon data are each included in the beacon data captured by the electronic bridge device during a given time period. Based on this, the server may determine that the patient associated with the patient ID included in the patient beacon data should be associated with the diagnostic information included in the diagnostic beacon data. As another example, the server may determine that locations of patients and/or pieces of equipment represented in the subsets of beacon data for a given time period should be set as the location of the electronic bridge device during that time period.

At step 410, the server stores the beacon data in accordance with the identified associations. For example, the server may update one or more databases (e.g., patient databases, temperature databases, diagnostic databases, equipment databases, and/or the like) stored in a memory device of the server to include entries containing groups of associated data elements. For example, the data elements may include room IDs, room names or numbers, patient IDs, patient names, equipment IDs, equipment names, sensor data (e.g., temperature data, light data, humidity data, and/or the like), device health data, and/or diagnostic data (e.g., EKG/ECG readings, and/or vital signs such as heart rate, body temperature, blood pressure, respiratory rate, and/or the like). For example, responsive to determining an association between a patient and diagnostic data in step 408, the server may update a patient database and/or a diagnostic database to include database entries that identify both the patient and the diagnostic data. As another example, responsive to determining associations between patients and/or equipment and the location of the electronic bridge device, the server may update one or more databases to include database entries indicating that such patients and/or equipment were located at the location of the electronic bridge device at a given time or during a given time period.

Figure 5:
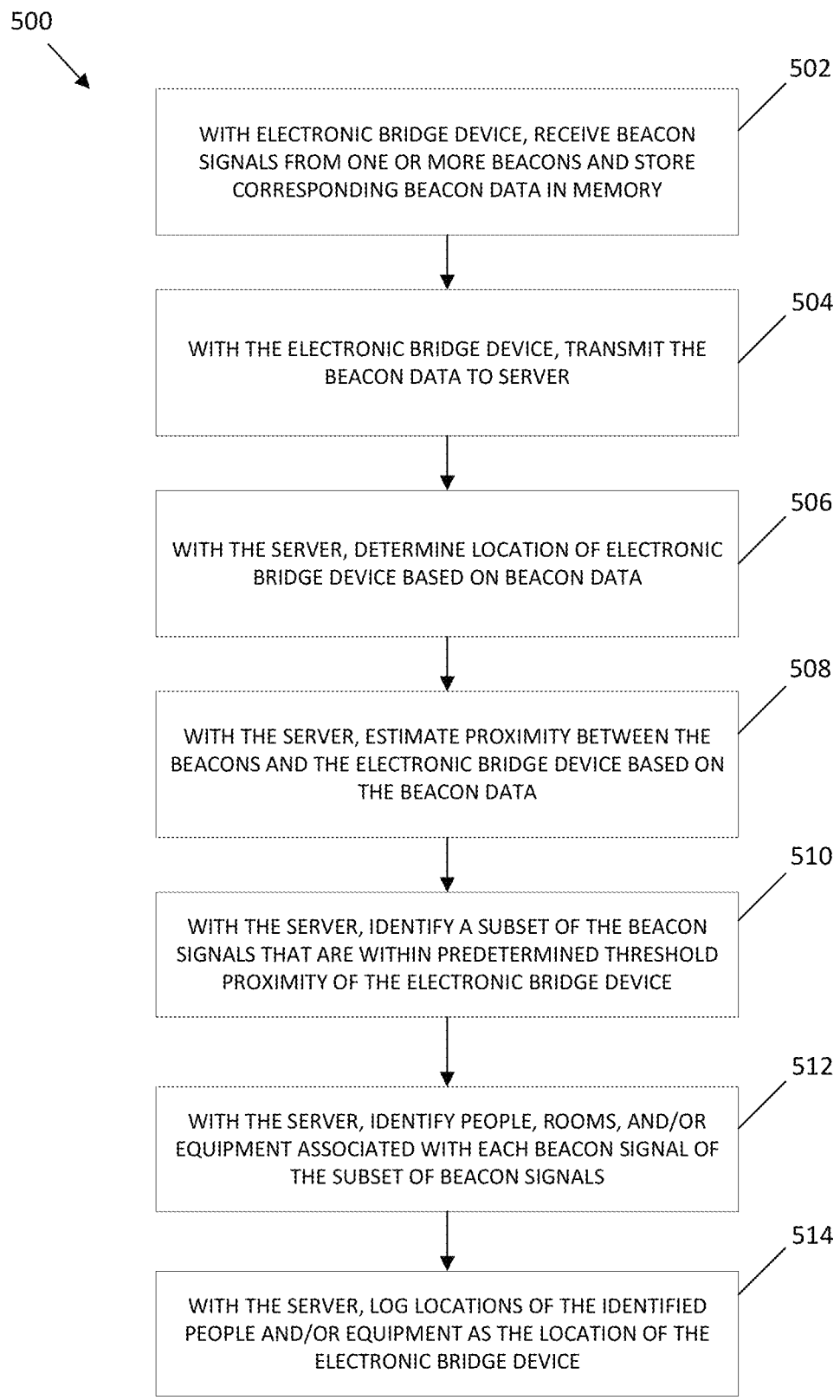
FIG. 5 shows an illustrative process flow for a method by which locations of people and/or equipment may be determined by an asset tracking system, in accordance with an embodiment.

FIG. 5 shows an illustrative process flow of a method 500 by which data ("beacon data") may be collected from beacons (e.g., beacons 108, 110, 112, 114, 128, 130, 132, 134, 202, 204, 206, 208, 210, FIGS. 1, 2) by an electronic bridge device (e.g., mobile device 106, laptop 116, laptop 212, FIGS. 1, 2), and may be sent to, analyzed, processed, and stored by a server (e.g., servers 140, FIG. 1) in order to determine approximate locations of people and/or equipment within a predetermined proximity threshold of the electronic bridge device. The method 500 may, for example be performed via the execution of computer-readable instructions via one or more computer processors (e.g., processors 302, FIG. 3), which may be included in one or more computer servers (e.g., server 140, FIG. 1). The steps of the method 500 are described as being performed using one such processor, though it should be understood that multiple processors may be used.

At step 502, the electronic bridge device receives beacon signals from one or more beacons, and stores corresponding beacon data in memory. For example, the beacons may include room beacons, equipment beacons, and/or patient beacons. The descriptions of the beacon signals and beacon data provided in the example of FIG. 4 are applicable to those of method 500, and are not repeated for the sake of brevity. For example, the electronic bridge device may receive the beacon signals via one or several WPAN connections (e.g., Bluetooth®/BLE).

At step 504, the electronic bridge device transmits the beacon data to one or more computer servers (e.g., server 140, FIG. 1; referred to henceforth as "the server"). For example, the electronic bridge device may transmit the data to the server(s) via a wireless connection to a LAN and/or via a WAN or the internet.

At step 506, the server determines a location of the electronic bridge device. In some embodiments, the electronic bridge device may have a static location that is known by (e.g., stored in a memory device of) the server. In some embodiments, the static location of the electronic bridge device may be represented as a room ID corresponding to the room in which the electronic bridge device is known to be located. In other such embodiments, the static location of the electronic bridge device may not be associated with a particular room, but may be associated with another feature of the facility (e.g., a nurse's station).

In some alternate embodiments, the electronic bridge device may be portable (e.g., a smartphone, tablet, laptop, and/or the like), and the location of the electronic bridge device may be determined (e.g., approximated) based on a room beacon signal received by the electronic bridge device (e.g., according to the method 600 of FIG. 6). For example, the server may determine that the location of the electronic bridge device is the room associated with the room ID included in the room beacon data included in the room beacon signal having the highest received signal strength indicator (RSSI) among room beacon signals received by the electronic bridge device.

At step 508, the server estimates the proximity between the electronic bridge device and each beacon to which the received beacon signals correspond. For example, the RSSI value of each beacon signal may be used as a basis for estimating proximity in this way. In alternate embodiments, the raw RSSI value may be used as the measure of proximity between the electronic bridge device and the identified people and/or equipment. The RSSI value for a given beacon signal may be measured by the electronic bridge device upon receipt of the beacon signal, and may be provided to the server along with the beacon data.

At step 510, the server identifies a subset of the beacon signals that correspond to beacons (e.g., and therefore patients and/or equipment) within a proximity threshold from the electronic bridge device. For example, the server may compare a proximity value derived from the RSSI value (or the RSSI value itself) of a given beacon signal to a predetermined threshold. If the proximity value of the beacon signal exceeds the predetermined threshold (e.g., indicating that the beacon signal is sufficiently strong), the server may determine that the corresponding beacon, and therefore the person or piece of equipment with which that beacon is associated, likely shares the approximate location of the electronic bridge device. Each beacon signal having a corresponding proximity value that exceeds the proximity threshold may be added to the subset of beacon signals. In some embodiments, the server may additionally or alternatively identify sets of beacon data that were included in the subset of beacon signals determined by the server to have exceeded the proximity threshold.

At step 512, the server analyzes the beacon data and identifies people and/or equipment associated with respective sets of beacon data associated with the identified subsets of the beacon signals. For example, the server may access a look-up table or other database stored in a memory of the server, which may define associations between people, rooms, and/or equipment and various patient IDs, equipment IDs, and/or temperature sensor beacon IDs, respectively. The server may then reference the patient IDs, equipment IDs, and/or temperature sensor beacon IDs included in the subsets of beacon data against the database to determine which patients and/or equipment are associated with each of the sets of beacon data that are associated with the identified subsets of the beacon signals.

At step 514, the server logs locations of the identified people and/or equipment as being the location of the electronic bridge device that was determined at step 506. For example, the server may maintain a database of locations of various people (e.g., patients) and equipment. Each time a new location is determined for a person or piece of equipment, a new database entry may be added by the server. In some embodiments, the database may maintain a table that stores only the current location of a given person or piece of equipment. For example, the server may update such a table, to replace a previous location of a person or piece of equipment stored in the table with the new location of that person or piece of equipment.

For example, each database entry may define at least a person or piece of equipment, a location, and one or more timestamps defining the time at which the corresponding beacon signal or signals were received.

FIG. 6 shows an illustrative process flow of a method 600 by which data ("beacon data") may be collected from two room beacons (e.g., beacons 102, 104, 202, FIGS. 1, 2) by an electronic bridge device (e.g., electronic bridge device 106, 116, laptop 212, FIGS. 1, 2), and may be sent to, analyzed, processed, and stored by a server (e.g., servers 140, FIG. 1) in order to determine the location of the electronic bridge device. The method 600 may, for example be performed via the execution of computer-readable instructions via one or more computer processors (e.g., processors 302, FIG. 3), which may be included in one or more computer servers (e.g., server 140, FIG. 1). The steps of the method 600 are described as being performed using one such processor, though it should be understood that multiple processors may be used. For example, the method of FIG. 6 may be executed when the electronic bridge device is a portable device (e.g., mobile device, smart phone, tablet, laptop, and/or the like) that is in proximity to at least one room beacon.

At step 602, the electronic bridge device receives at least one room beacon signal from at least one room beacon. The electronic bridge may measure at least one RSSI value of the at least one room beacon signal, and may add the at least one RSSI value to corresponding room beacon data included in the at least one room beacon signal. The descriptions of the room beacon signals and the room beacon data provided in the example of FIG. 4 are applicable to those of method 600, and are not repeated for the sake of brevity. For example, the electronic bridge device may receive the first and second room beacon signals via one or several WPAN connections (e.g., Bluetooth®/BLE).

For example, the electronic bridge device may receive a first room beacon signal from a first room beacon and may store corresponding first room beacon data in memory. The electronic bridge device may then receive a second room beacon signal from a second room beacon and may store corresponding second room beacon data in memory. The first room beacon data may include a first room ID associated with a first room. The electronic bridge device may measure a first RSSI value of the first room beacon signal, and may add the first RSSI value to the first room beacon data. The second room beacon data may include a second room ID associated with a second room. The electronic bridge device may measure a second RSSI value of the second room beacon signal, and may add the second RSSI value to the second room beacon data.

At step 604, the electronic bridge device transmits the room beacon data received by the electronic bridge device to one or more computer servers (e.g., server 140, FIG. 1; referred to henceforth as "the server"). For example, the electronic bridge device may transmit the data to the server(s) via a wireless connection to a LAN and/or via a WAN or the internet.

For example, the electronic bridge device may send the first room beacon data and the second room beacon data (e.g., including the first and second RSSI values, respectively) to the server.

At step 606, the server identifies a room beacon signal having the highest RSSI value of the room beacon signals received by the electronic bridge device (e.g., of those room beacon signals received by the electronic bridge device during a given time period).

For example, the server may compare the first RSSI value of the first room beacon signal to the second RSSI value of the second room beacon signal, and may determine that the first RSSI value is higher than the second RSSI value.

At step 608, identifies a location associated with a room ID included in the room beacon data of the identified room beacon signal.

For example, the server may access a look-up table or other database stored in a memory of the server, which may define associations between locations and room IDs. Responsive to determining that the first RSSI value is higher than the second RSSI value, the server may reference the first room ID that is included in the first room beacon data against the database to determine which location (e.g., room) corresponds to the first room ID.

At step 610, the server sets the approximate location of the electronic bridge device as being that of the room. For example, the server may maintain a database or other record of the location of the electronic bridge device (e.g., as the device moves from room to room over time). Each time a new location is determined for the electronic bridge device, a corresponding database entry may be added by the server, which may include the time at which the approximate location of the electronic bridge device was determined or the time at which the first room beacon signal was received by the electronic bridge device. In this way, a record of the approximate location of the electronic bridge device may be maintained.

Figure 7:
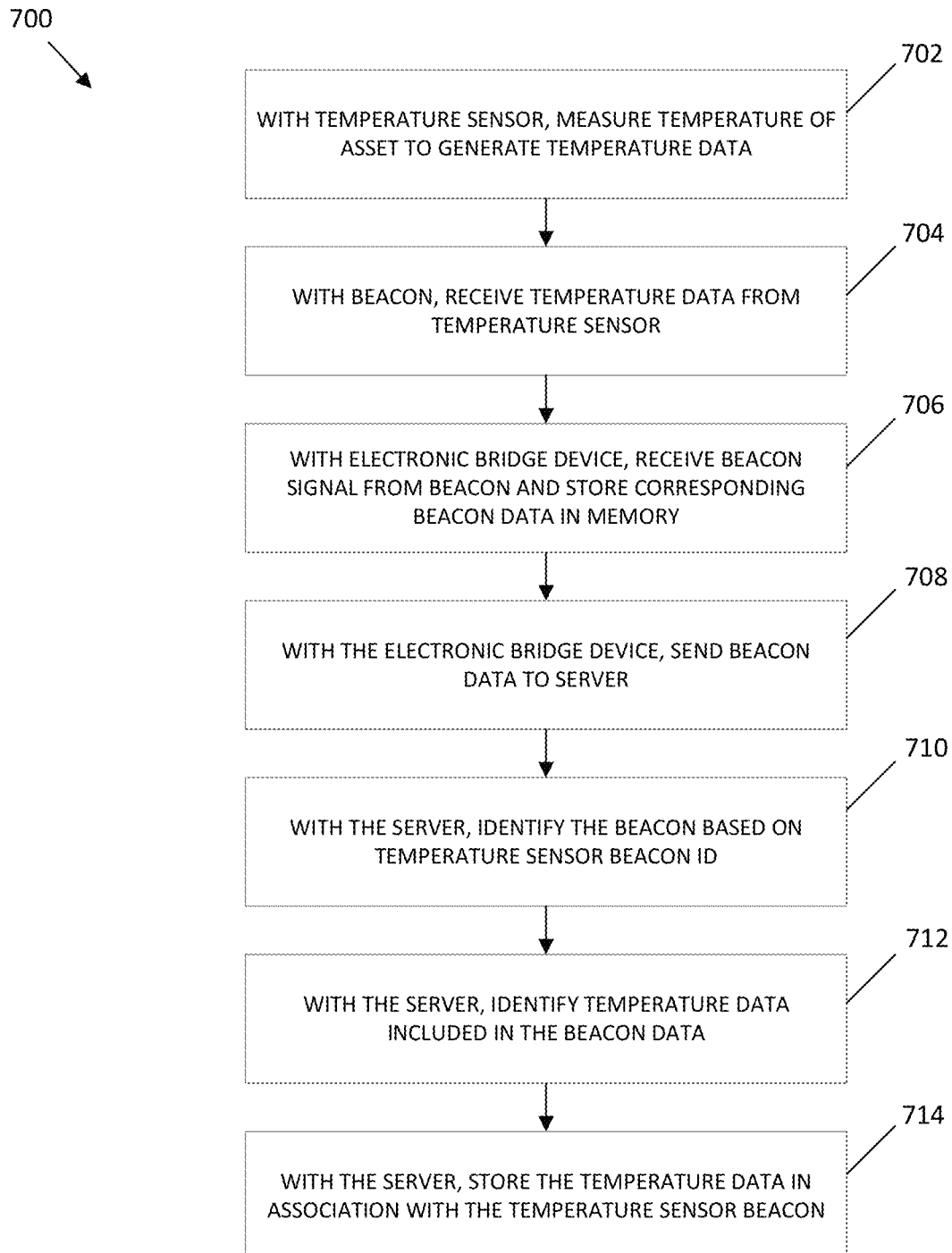
FIG. 7 shows an illustrative process flow for a method by which temperature data may be collected by an electronic bridge device of an asset tracking system, in accordance with an embodiment.

FIG. 7 shows an illustrative process flow of a method 700 by which temperature data may generated by a temperature sensor, and may be broadcast by a temperature sensor beacon (e.g., beacon 112, FIG. 1) and received by an electronic bridge device (e.g., electronic bridge device 106, 116, laptop 212, FIGS. 1, 2). The temperature data may be sent to, analyzed, processed, and stored by a server (e.g., servers 140, FIG. 1), where the temperature data may be associated with a device at which the temperature was measured by the temperature sensor. The method 700 may, for example be performed via the execution of computer-readable instructions via one or more computer processors (e.g., processors 302, FIG. 3), which may be included in one or more computer servers (e.g., server 140, FIG. 1). The steps of the method 700 are described as being performed using one such processor, though it should be understood that multiple processors may be used.

At step 702, the temperature sensor measures the temperature of an asset or a patient and generates temperature data that includes measured temperature values and corresponding time stamps. For example, the temperature sensor may measure an ambient temperature within a temperature-controlled device such as a refrigerator or freezer, or another piece of equipment that may require temperature monitoring. As another example, the temperature sensor may measure a surface temperature of a patient's skin.

At step 704, the temperature sensor beacon receives the temperature data from the temperature sensor. For example, the temperature sensor beacon may be directly coupled to the temperature sensor via a wired connection, and the temperature data may be sent to the temperature sensor beacon by the temperature sensor via this connection. In some embodiments, the temperature sensor may instead be included in the temperature sensor beacon (e.g., completely or partially within a housing of the temperature sensor beacon) and may be coupled to a microcontroller or processor of the temperature sensor beacon via a wired connection and/or via conductive traces of a printed circuit board on which the microcontroller or processor is disposed, and the temperature data may be sent to the microcontroller or processor by the temperature sensor via this connection. The temperature sensor beacon may generate temperature sensor beacon data that includes the temperature data and, in some embodiments, a temperature sensor beacon ID (e.g., a MAC address of the temperature sensor beacon) that uniquely identifies the temperature sensor beacon.

At step 706, the electronic bridge device receives temperature sensor beacon signals transmitted (e.g., broadcast) by the temperature sensor beacon. For example, the electronic bridge device may receive the temperature sensor beacon signals via one or several WPAN connections (e.g., Bluetooth®/BLE). The temperature sensor beacon signals include the temperature sensor beacon data. The electronic bridge device stores the temperature sensor beacon data included in the temperature sensor beacon signals in memory. The descriptions of the temperature sensor beacon signals and temperature sensor beacon data provided in the example of FIG. 4 are applicable to those of method 700, and are not entirely repeated for the sake of brevity.

At step 708, the electronic bridge device sends the beacon data to one or more computer servers (e.g., server 140, FIG. 1; referred to henceforth as "the server"). For example, the electronic bridge device may transmit the data to the server via a wireless connection to a LAN and/or via a WAN or the internet.

At step 710, the server analyzes the temperature sensor beacon data to identify the portion of the beacon data corresponding to the temperature sensor beacon ID. The temperature sensor beacon may then be identified by the server based on the temperature sensor beacon ID. For example, the server may access a look-up table or other database stored in a memory device of the server, which may define associations between temperature sensor beacon IDs and temperature sensor beacons. The server may then reference the temperature sensor beacon ID against the database to determine which temperature sensor beacon corresponds to the temperature sensor beacon and, therefore, the temperature data included in the temperature sensor beacon data.

The server may additionally identify one or more locations and/or pieces of equipment associated with the identified temperature sensor beacon at this step. For example, the server may store a temperature sensor database that defines relationships between temperature sensor beacons, equipment (e.g., refrigerators, freezers, and/or the like), and locations. For a given temperature sensor beacon, the temperature sensor database may include a record of the equipment in or on which that temperature sensor beacon is disposed and/or a record of the location of the equipment and/or the temperature sensor beacon.

At step 712, the server analyzes the beacon data to identify the portion of the beacon data corresponding to the temperature data.

At step 714, the server stores the temperature data in a memory device of the server in association with the temperature sensor beacon identified at step 710. For example, the memory device of the server may include a temperature database in which temperature sensor data collected from various temperature sensors and/or temperature sensor beacons is stored. When temperature data is received by the server from a given temperature sensor beacon, as described above, the server may update the portion of the database corresponding to that temperature sensor beacon to include the received temperature data. In some embodiments, the server may additionally or alternatively associate the temperature data with the equipment at or within which the temperature was measured in order to generate the temperature data. In this way, the temperature at or within a piece of equipment may be monitored over time, and may be stored for future analysis.

In some embodiments, the server may monitor the temperature data corresponding to a given piece of equipment. The server may determine that a temperature of the temperature data has exceeded a predetermined threshold for longer than a predefined time period and, in response, may cause an alert to be sent to one or more user devices (e.g., user devices 106, FIG. 1). The alert may notify the recipient(s) that the temperature has exceeded the predefined threshold. In some embodiments, the alert may require a response from the user device(s) that received the alert. For example, the recipient may be required to send a response to the server, indicating that some action has been taken to resolve the temperature overage.

Figure 8:
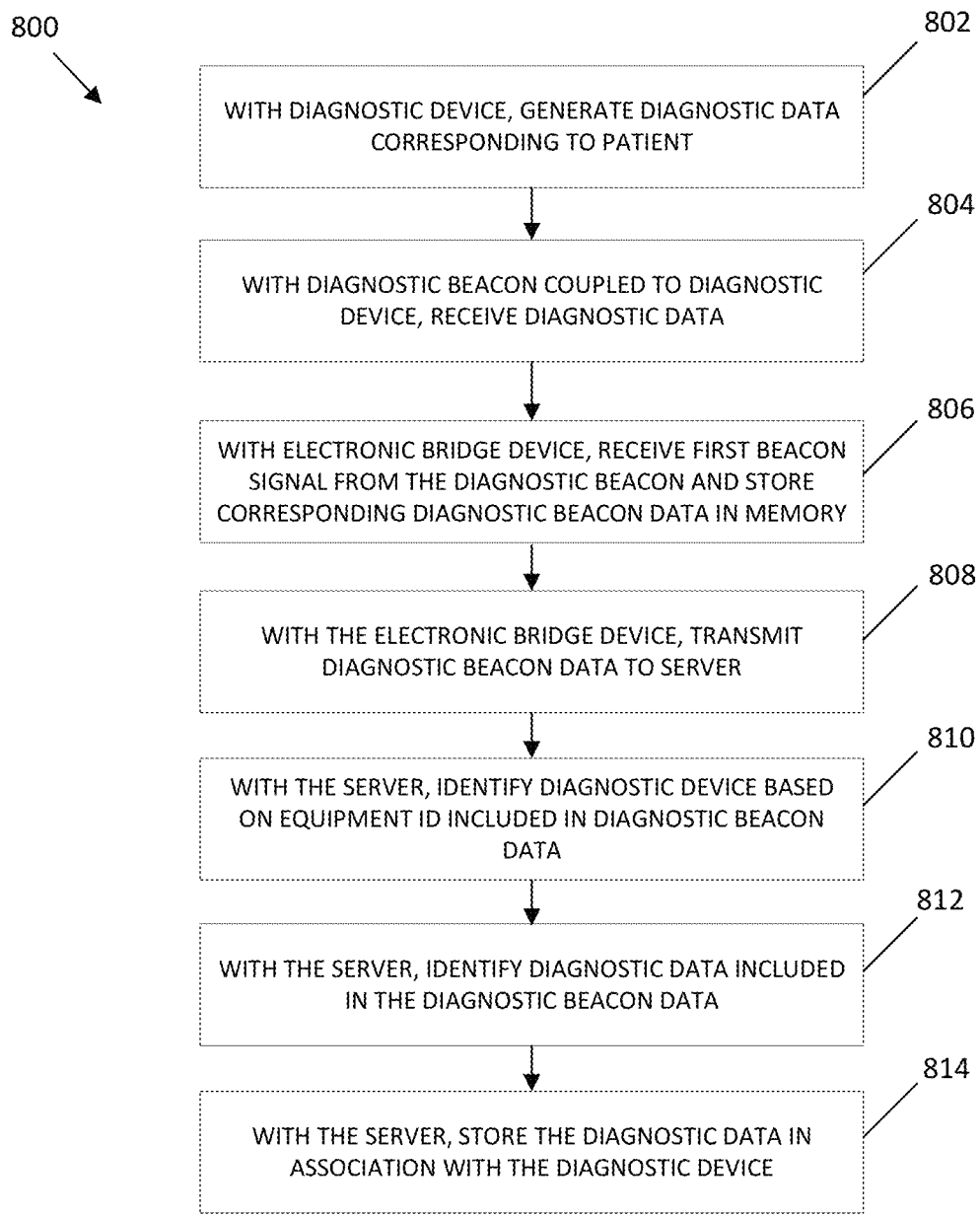
FIG. 8 shows an illustrative process flow for a method by which characteristic data may be collected by an electronic bridge device of an asset tracking system, in accordance with an embodiment.

FIG. 8 shows an illustrative process flow of a method 800 by which data (e.g., diagnostic beacon data and patient beacon data) may be collected from beacons (e.g., beacons 108, 110, 112, 114, 128, 130, 132, 134, 202, 204, 206, 208, 210, FIGS. 1, 2) by an electronic bridge device (e.g., electronic bridge device 106, 116, laptop 212, FIGS. 1, 2), and may be sent to, analyzed, processed, and stored by a server (e.g., servers 140, FIG. 1). The diagnostic beacon data may include diagnostic data that includes measurements taken by a diagnostic device, and an equipment ID for the diagnostic device. The patient beacon data may include a patient ID associated with a patient, where the measurements included in the diagnostic data are taken from the patient. The server may update one or more databases to associate the diagnostic data with the diagnostic device that generated the diagnostic data and to associate the diagnostic data with the patient to which the diagnostic data corresponds (i.e., from whom the diagnostic data was acquired). The method 800 may, for example be performed via the execution of computer-readable instructions via one or more computer processors (e.g., processors 302, FIG. 3), which may be included in one or more computer servers (e.g., server 140, FIG. 1). The steps of the method 800 are described as being performed using one such processor, though it should be understood that multiple processors may be used in some embodiments.

At step 802, the diagnostic device generates diagnostic data by measuring one or more characteristics of a patient. The diagnostic data may include one or more diagnostic values (e.g., values of body temperature, pulse, pulse oximetry, blood pressure, respiration rate, EKG/ECG readings, and/or the like) and time stamps corresponding to the time at which each measurement was obtained.

At step 804, a diagnostic beacon (e.g., diagnostic beacon 132, FIG. 1) receives the diagnostic data from the medical diagnostic device. For example, the diagnostic beacon may be directly coupled to the medical diagnostic device via a wired connection, and the diagnostic data may be sent to the diagnostic beacon by the temperature sensor via this connection. In some embodiments, the medical diagnostic device and the diagnostic beacon may be included in a single, integrated device. The diagnostic beacon generates diagnostic beacon data and transmits (e.g., broadcasts) the diagnostic beacon data. The diagnostic beacon data may include the diagnostic data and an equipment ID (e.g., a MAC address of the diagnostic beacon) associated with the diagnostic device.

In some such embodiments, sensing/measurement devices of the medical diagnostic device may be coupled to a microcontroller or processor (e.g., which may be shared between the medical diagnostic device and the diagnostic beacon) of the integrated device via a wired connection and/or via conductive traces of a printed circuit board on which the microcontroller or processor is disposed, and the diagnostic data may be sent to the microcontroller or processor by the sensing/measurement devices via this connection before being wirelessly broadcast/transmitted via one or more antennas of the diagnostic beacon.

In other such embodiments, the separate microcontrollers and/or processors for each of the medical diagnostic device and the diagnostic beacon may be included in the integrated device, and the diagnostic may be passed from the sensing/measurement devices to a diagnostic microcontroller/processor of the medical diagnostic device, to a second microcontroller/processor of the diagnostic beacon, and finally to transmit/receive circuitry of the diagnostic beacon for transmission/broadcast via one or more antennas of the diagnostic beacon.

At step 806, the electronic bridge device receives a first beacon signal ("diagnostic beacon signal") from the diagnostic beacon, which includes the diagnostic beacon data. The electronic bridge device stores the diagnostic beacon data in a memory device. The description of the diagnostic beacon signals and diagnostic beacon data provided in the example of FIG. 4 are applicable to those of method 800, and are not repeated for the sake of brevity. For example, the electronic bridge device may receive the beacon signals via one or several WPAN connections (e.g., Bluetooth®/BLE).

In some embodiments, the electronic bridge device may receive other beacon signals, such as room beacon signals and patient beacon signals at step 806. Such room beacon signals may be used to identify the location of the electronic bridge device (e.g., according to method 600 of FIG. 6). The patient beacon signal may be used to identify a patient (e.g., as described in connection with method 400 of FIG. 4).

At step 808, the electronic bridge device transmits the diagnostic beacon data and the patient beacon data to one or more computer servers (e.g., server 140, FIG. 1; referred to henceforth as "the server"). For example, the electronic bridge device may transmit the data to the server(s) via a wireless connection to a LAN and/or via a WAN or the internet. In some embodiments, the electronic bridge device may also transmit other beacon data (e.g., patient beacon data, room beacon data, and/or the like) received during the same time period at this step.

At step 810, the server analyzes the diagnostic beacon data to identify the portion of the diagnostic beacon data corresponding to an equipment ID. The diagnostic device to which the equipment ID corresponds is then identified by the server. For example, the server may access a look-up table or other database stored in a memory device of the server, which may define associations between equipment and equipment IDs. The server may then reference the equipment ID included in the diagnostic beacon data against the database to determine the piece of equipment (i.e., the diagnostic device) that corresponds to the equipment ID and, therefore, the diagnostic beacon data.

At step 812, the server analyzes the diagnostic beacon data to identify the portion of the diagnostic beacon data corresponding to the diagnostic data.

At step 814, the server stores the diagnostic data in a memory device of the server in association with the diagnostic device identified at step 812. In some embodiments, the server may additionally or alternatively store the diagnostic data in the memory device of the server in association with a patient (e.g., identified as corresponding to patient beacon data received by the electronic bridge device during the same time period) and/or a location (e.g., the location of the electronic bridge device during the same time period, which may be static or determined based on a room beacon signal, as described above). For example, the memory device of the server may include a diagnostic database that stores diagnostic data. When diagnostic data is received by the server for a given diagnostic device, as described above, the server may update the portion of the database corresponding to that diagnostic device to include the received diagnostic data. Database entries corresponding to the diagnostic data may be further associated with a patient and/or location, in some embodiments.

In some embodiments, the server may monitor the diagnostic data corresponding to a given patient. The server may determine that a diagnostic value has exceeded a predetermined threshold for longer than a predefined time period and, in response, may cause an alert to be sent to one or more user devices (e.g., user devices 106, FIG. 1). The alert may notify the recipient(s) that the diagnostic value has exceeded the predefined threshold. In some embodiments, the alert may require a response from the user device(s) that received the alert. For example, the recipient may be required to send a response to the server indicating that some action has been taken to resolve the diagnostic value exceeding the predetermined threshold.

It should be understood that any or all of the methods 400, 500, 600, 700, 800 of FIGS. 4, 5, 6, 7, and 8 may be performed in any applicable combination with one another, such that various types of beacons (e.g., beacons 108, 110, 112, 114, 128, 130, 132, 134, 202, 204, 206, 208, 210, FIGS. 1, 2) and corresponding beacon data may be collected and analyzed by a given electronic bridge device (e.g., electronic bridge device 106, 116, laptop 212, FIGS. 1, 2) and one or more computer servers (e.g., servers 140, FIG. 1) simultaneously or near-simultaneously.

EXAMPLES

In an example use-case of the present asset tracking system, room beacons and equipment beacons may be utilized in combination with one or more electronic bridge devices and/or servers (e.g., using the method 500 of FIG. 5) to maintain a record of the sizes of various hospital beds and the rooms in which those beds are located within a hospital. For example, such a record of associations between hospital beds and rooms may be analyzed when assigning a room to a patient in order to avoid that patient being erroneously assigned to a room that contains a bed that is the wrong size for that patient.

In another example use-case of the present asset tracking system, personal locating beacons may be worn by doctors and nurses as well as by patients, and a record of the locations of such doctors, nurses, and patients may be tracked throughout various time periods. For example, such a record of the locations of doctors, nurses, and patients (e.g., with such locations being determined according to the method 500 of FIG. 5) may enable a time-motion study to be performed (e.g., automatically by one or more computers/servers and/or manually) to assess the efficiencies of tasks performed by or in relation to such individuals.

In another example use-case of the present asset tracking system, the locations of various pieces of equipment may be tracked using equipment beacons (e.g., equipment beacons 110, 130), electronic bridge devices (e.g., electronic bridge devices 106, 116), and one or more servers (e.g., servers 140). The server(s) may monitor one or more equipment databases (e.g., of databases 142, FIG. 1) that store the locations of various devices, assets, and/or pieces of equipment, as determined by the tracking system. The server(s) may compare a location for a given device to an expected location for that device, or to a rule or set of rules defining locations that the device is either authorized to be in or is not authorized to be in. If the server(s) determine that the given device is at an unexpected or unauthorized location, then an alert may be sent to one or more user devices (e.g., user devices 106, FIG. 1). In some embodiments, the recipient(s) of the alert via user device(s) may be required to send a response to the servers, indicating an action taken by the recipient to resolve the issue (e.g., returning the device to an expected or authorized location). For example, the device may be an electronic tablet device that is only authorized to be located in a single patient room, per rules defined in a memory device of the server. If the electronic tablet device is determined by the server, based on location data generated by the tracking system, to be in any location other than the single patient room, then an alert may be sent to a user device of a staff member or administrator. As another example, the device may be a piece of medical equipment, such as a ventilator or a pump configured to deliver medicine to a patient. The medical equipment may only be authorized to be in the same room as a corresponding patient, per a rule defined in the memory of the server. If the server determines that the patient and the medical equipment are in different rooms, the server may cause a corresponding alert to be sent to a user device of a staff member or administrator.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

I claim:

1. A tracking system, comprising:
a first beacon that includes a room beacon disposed at a fixed location within a first room, the first beacon being configured to wirelessly broadcast a first beacon signal including first beacon data that includes room beacon data;
a second beacon configured to wirelessly broadcast a second beacon signal including second beacon data;
an electronic bridge device configured to:
receive the first beacon signal and the second beacon signal, and
store the first beacon data and the second beacon data; and
a server in electronic communication with the electronic bridge device, the server comprising:
a processor, and
a memory device configured to store computer-readable instructions that, when executed, cause the processor to:
receive the first beacon data including the room beacon data and the second beacon data from the electronic bridge device;
determine a location of the electronic bridge device based on the room beacon data;
determine that the second beacon is associated with the location of the electronic bridge device; and
store the first beacon data, the second beacon data, and an association of the second beacon data with the location of the electronic bridge device in the memory device.

2. The tracking system of claim 1, wherein the room beacon data comprises a room identifier, and wherein the computer-readable instructions, when executed, further cause the processor to:
reference the room identifier against a first database of the memory device to determine the location, wherein the first database defines a first plurality of associations between room identifiers and locations, wherein the location corresponds to the first room.

3. The tracking system of claim 2, wherein the second beacon comprises a patient beacon that is configured to be worn by a patient, wherein the second beacon data comprises a patient identifier associated with the patient, and wherein the computer-readable instructions cause the processor to:
reference the patient identifier against a second database of the memory device to identify the patient, wherein the second database defining a second plurality of associations between patient identifiers and patients; and
update the memory device to associate the patient with the location of the electronic bridge device.

4. The tracking system of claim 2, further comprising a third beacon that includes an equipment beacon that is disposed on a medical device, wherein the third beacon is configured to wirelessly broadcast a third beacon signal that includes an equipment identifier, and wherein the computer-readable instructions cause the processor to:
reference the equipment identifier against a third database of the memory device to identify the medical device, the third database defining a third plurality of associations between equipment identifiers and equipment; and
update the memory device to associate the medical device with the location of the electronic bridge device.

5. The tracking system of claim 4, wherein the medical device includes a diagnostic device configured to generate diagnostic data and the third beacon signal includes the diagnostic data.

6. The tracking system of claim 5, wherein the computer-readable instructions cause the processor to:
reference the room beacon data against a fourth database of the memory device to identify a patient identifier; and
update the memory device to define the diagnostic data as being associated with both the diagnostic device and the patient identifier.

7. The tracking system of claim 2, wherein the room beacon data is first room beacon data, wherein the electronic bridge device is configured to determine a first received signal strength indicator (RSSI) value corresponding to a first received signal strength of the first room beacon signal as measured by the electronic bridge device, wherein the electronic bridge device is configured to send the first RSSI value to the server, and wherein the tracking system further comprises:
a second room beacon disposed at a second fixed location within a second room, the second room beacon being configured to wirelessly broadcast a second room beacon signal comprising second room beacon data that includes a second room identifier associated with the second room, wherein the electronic bridge device is configured to determine a second RSSI value corresponding to a second received signal strength of the second room beacon signal as measured by the electronic bridge device, wherein the electronic bridge device is configured to send the second RSSI value and the second room beacon data to the server, and wherein the computer-readable instructions, when executed, further cause the processor to:
compare the first RSSI value to the second RSSI value;
determine that the first RSSI value exceeds the second RSSI value; and update the memory device to set the first room as the location of the electronic bridge device.

8. The tracking system of claim 1, further comprising:
a temperature sensor coupled to the second beacon and configured to generate temperature data, wherein the second beacon receives the temperature data from the temperature sensor, and wherein the second beacon data comprises the temperature data and a temperature sensor beacon identifier and wherein the computer-readable instructions, when executed, further cause the processor to:
update the memory device to define the temperature data as being associated with the second beacon.

9. The tracking system of claim 1, wherein the electronic bridge device is wirelessly coupled to the first beacon and to the second beacon via at least one wireless personal area network, and wherein the electronic bridge device is communicatively coupled to the server via a wide area network.

10. The tracking system of claim 1, wherein the electronic bridge device is a general-purpose computing device including a laptop computer, a tablet computer, or a desktop computer.

11. A system, comprising:
a first beacon associated with a medical device, the first beacon being configured to wirelessly broadcast a first beacon signal that includes an equipment identifier;
a second beacon configured to wirelessly broadcast a second beacon signal comprising second beacon data;
an electronic bridge device configured to:
receive the first beacon signal and the second beacon signal, and
store the first beacon data and the second beacon data; and
a server in electronic communication with the electronic bridge device, the server comprising a processor; and
a memory device configured to store computer-readable instructions that, when executed, cause the processor to:
receive the first beacon data and the second beacon data from the electronic bridge device; and
update a database of the memory device to associate the medical device with the second beacon data.

12. The system of claim 11, wherein the first beacon signal includes diagnostic data generated by the medical device, the second beacon data includes a patient identifier, and the computer-readable instructions, when executed, cause the processor to:
store the diagnostic data in the memory device; and
update the database of the memory device to associate with the diagnostic data with the patient identifier.

13. The system of claim 12, wherein the computer-readable instructions, when executed, cause the processor to:
determine that a diagnostic data value in the diagnostic data has exceeded a predetermined threshold; and
cause an alert to be sent to a user device, the alert indicating that the predetermined threshold has been exceeded.

14. A method, comprising:
broadcasting, by a first beacon that includes a room beacon disposed at a fixed location within a first room, a first beacon signal that includes first beacon data that includes room beacon data;
broadcasting, by a second beacon, a second beacon signal including second beacon data;
receiving, by an electronic bridge device, the first beacon signal and the second beacon signal;
storing, by the electronic bridge device, the first beacon data and the second beacon data;
receiving, by a server in electronic communication with the electronic bridge device, the first beacon data including the room beacon data and the second beacon data from the electronic bridge device;
determining, by the server, a location of the electronic bridge device based on the room beacon data;
determining, by the server, that the second beacon is associated with the location of the electronic bridge device; and
storing, by the server, the first beacon data, the second beacon data, and an association of the second beacon data with the location of the electronic bridge device in a memory device.

15. The method of claim 14, wherein the room beacon data comprises a room identifier, and further comprising:
referencing, by the server, the room identifier against a first database of the memory device to determine the location, wherein the first database defines a first plurality of associations between room identifiers and locations, wherein the location corresponds to the first room.

16. The method of claim 15, wherein the second beacon comprises a patient beacon that is configured to be worn by a patient, wherein the second beacon data comprises a patient identifier associated with the patient, and further comprising:
referencing, by the server, the patient identifier against a second database of the memory device to identify the patient, wherein the second database defining a second plurality of associations between patient identifiers and patients; and
updating, by the server, the memory device to associate the patient with the location of the electronic bridge device.

17. The method of claim 15, further comprising:
broadcasting, by a third beacon that includes an equipment beacon that is disposed on a medical device, a third beacon signal that includes an equipment identifier;
receiving, by the server, the third beacon signal;
referencing, by the server, the equipment identifier against a third database of the memory device to identify the medical device, the third database defining a third plurality of associations between equipment identifiers and equipment; and
updating, by the server, the memory device to associate the medical device with the location of the electronic bridge device.

18. The method of claim 17, wherein the medical device includes a diagnostic device configured to generate diagnostic data and the third beacon signal includes the diagnostic data.

19. The method of claim 18, further comprising:
referencing the room beacon data against a fourth database of the memory device to identify a patient identifier; and
updating, by the server, the memory device to define the diagnostic data as being associated with both the diagnostic device and the patient identifier.

20. The method of claim 14, wherein the electronic bridge device is a general-purpose computing device including a laptop computer, a tablet computer, or a desktop computer.

* * * * *